US011306400B2

(12) United States Patent
Rane et al.

(10) Patent No.: US 11,306,400 B2
(45) Date of Patent: Apr. 19, 2022

(54) 2-SUBSTITUTED IMIDAZOLE AND BENZIMIDAZOLE CORROSION INHIBITORS

(71) Applicant: Ecolab USA Inc., St. Paul, MN (US)

(72) Inventors: Deepak Rane, Mumbai (IN); Jothibasu Seetharaman, Cuddalore (IN); Jeffery M. Atkins, Aurora, IL (US); Anand Harbindu, Shahjahanpur (IN); Piyush Anant, Jharkhand (IN); Vaideeswaran Sivaswamy, Pune (IN); Pradeep Cheruku, Bolingbrook, IL (US)

(73) Assignee: Ecolab USA Inc., St. Paul, MN (US)

( * ) Notice: Subject to any disclaimer, the term of this patent is extended or adjusted under 35 U.S.C. 154(b) by 609 days.

(21) Appl. No.: 16/225,293

(22) Filed: Dec. 19, 2018

(65) Prior Publication Data

US 2019/0136387 A1 May 9, 2019

Related U.S. Application Data

(63) Continuation of application No. 15/166,527, filed on May 27, 2016, now Pat. No. 10,202,694.
(Continued)

(51) Int. Cl.
*C23F 11/00* (2006.01)
*C23F 11/04* (2006.01)
(Continued)

(52) U.S. Cl.
CPC .......... *C23F 11/149* (2013.01); *C07D 231/12* (2013.01); *C07D 235/12* (2013.01);
(Continued)

(58) Field of Classification Search
CPC ....... C23F 11/182; C23F 11/00; C23F 11/149; C02F 1/00
(Continued)

(56) References Cited

U.S. PATENT DOCUMENTS 3,408,307 A  10/1968  Troscinski et al.
3,615,616 A  10/1971  Wilrijk et al.
(Continued)

FOREIGN PATENT DOCUMENTS

CN  1103651 A  6/1995
CN  1188589 A  7/1998
(Continued)

OTHER PUBLICATIONS

F. Zhang et al., Performance and Theoretical Study on Corrosion Inhibition of 2-(4-pyridyl)-benzimidazole for Mild Steel in Hydrochloric Acid, Corrosion Science, Apr. 3, 2012, V.61, pp. 1-9.*
(Continued)

*Primary Examiner* — Monzer R Chorbaji
(74) *Attorney, Agent, or Firm* — Leydig, Voit & Mayer, Ltd.

(57) ABSTRACT

Disclosed are methods of using nitrogen-containing compounds as corrosion inhibitors. The present method is used to inhibit corrosion of a metal surface in contact with an aqueous system using 2-substituted imidazoles and 2-substituted benzimidazoles, and provides enhanced protection against corrosion of metals in the aqueous system. The method comprises the use of corrosion inhibitors that are generally resistant to halogen attack and provide good corrosion resistance in the presence of oxidizing halogen-based biocides. Formulations comprising 2-substituted imidazoles and 2-substituted benzimidazoles are also disclosed.

20 Claims, 8 Drawing Sheets

Related U.S. Application Data

(60) Provisional application No. 62/167,697, filed on May 28, 2015.

(51) Int. Cl.

| | | |
|---|---|---|
| *B05D 1/30* | (2006.01) | |
| *B05D 1/02* | (2006.01) | |
| *C23F 11/14* | (2006.01) | |
| *C07D 235/12* | (2006.01) | |
| *C07D 401/04* | (2006.01) | |
| *C07D 231/12* | (2006.01) | |
| *C07D 235/30* | (2006.01) | |
| *C23F 11/18* | (2006.01) | |
| *C02F 103/02* | (2006.01) | |
| *C23F 11/12* | (2006.01) | |
| *C23F 11/173* | (2006.01) | |

(52) U.S. Cl.
CPC ......... *C07D 235/30* (2013.01); *C07D 401/04* (2013.01); *C23F 11/184* (2013.01); *C02F 2103/023* (2013.01); *C02F 2303/08* (2013.01); *C23F 11/124* (2013.01); *C23F 11/141* (2013.01); *C23F 11/173* (2013.01)

(58) Field of Classification Search
USPC .................... 422/7, 12–14, 16; 427/420, 427
See application file for complete search history.

(56) References Cited

U.S. PATENT DOCUMENTS

| | | | |
|---|---|---|---|
| 4,134,959 A | 1/1979 | Menke et al. | |
| 4,142,029 A | 2/1979 | Illy | |
| 4,306,986 A | 12/1981 | Schiessl | |
| 4,395,294 A | 7/1983 | Hobbins et al. | |
| 4,758,312 A | 7/1988 | Hunt et al. | |
| 5,082,611 A | 1/1992 | Adams et al. | |
| 5,128,065 A | 7/1992 | Hollander | |
| 5,156,769 A | 10/1992 | Cha et al. | |
| 5,382,367 A | 1/1995 | Zinkan et al. | |
| 5,455,220 A | 10/1995 | Dedolph | |
| 5,468,410 A | 11/1995 | Angevaare et al. | |
| 5,476,947 A | 12/1995 | Maki et al. | |
| 5,744,424 A | 4/1998 | Dedolph | |
| 5,746,947 A | 5/1998 | Vanderpool et al. | |
| 5,772,919 A | 6/1998 | Reichgott et al. | |
| 5,874,026 A | 2/1999 | Pilsits, Jr. et al. | |
| 6,103,144 A | 8/2000 | Cheng | |
| 6,203,719 B1 | 3/2001 | Turcotte et al. | |
| 6,379,587 B1 | 4/2002 | Chen | |
| 6,572,789 B1 | 6/2003 | Yang et al. | |
| 6,585,933 B1 * | 7/2003 | Ehrhardt ................. | C23F 11/08 252/180 |
| 6,646,082 B2 | 11/2003 | Ghosh et al. | |
| 6,696,437 B1 | 2/2004 | Lubisch et al. | |
| 7,393,395 B2 | 7/2008 | Aiba et al. | |
| 7,968,507 B2 | 6/2011 | Lee et al. | |
| 7,972,655 B2 | 7/2011 | Abys et al. | |
| 8,361,237 B2 | 1/2013 | Wu et al. | |
| 9,074,170 B2 | 7/2015 | Barnes et al. | |
| 2003/0063998 A1 | 4/2003 | Ghosh et al. | |
| 2003/0065116 A1 | 4/2003 | Ghosh et al. | |
| 2010/0123100 A1 | 5/2010 | Gill et al. | |
| 2010/0152086 A1 | 6/2010 | Wu et al. | |
| 2010/0163469 A1 | 7/2010 | Wan et al. | |
| 2010/0197136 A1 | 8/2010 | Shimada et al. | |
| 2011/0318929 A1 | 12/2011 | Mishima et al. | |
| 2012/0108489 A1 | 5/2012 | Miralles | |
| 2012/0283163 A1 | 11/2012 | Barnes et al. | |
| 2013/0295292 A1 | 11/2013 | Bukeikhanova et al. | |
| 2014/0044593 A1 | 2/2014 | Garner | |
| 2015/0152329 A1 | 6/2015 | Seetharaman et al. | |
| 2016/0032221 A1 | 2/2016 | Barnes et al. | |

FOREIGN PATENT DOCUMENTS

| | | |
|---|---|---|
| CN | 1057350 C | 10/2000 |
| CN | 1280606 A | 1/2001 |
| CN | 1359430 A | 7/2002 |
| CN | 1758144 A | 4/2006 |
| CN | 102334022 A | 1/2012 |
| CN | 102888208 A | 1/2013 |
| CN | 103436888 A | 12/2013 |
| CN | 103443329 A | 12/2013 |
| CN | 103641248 A | 3/2014 |
| EP | 0226016 A1 | 11/1986 |
| EP | 0215670 A2 | 3/1987 |
| EP | 0634460 A2 | 1/1995 |
| EP | 1288232 A2 | 3/2003 |
| EP | 2199379 A1 | 6/2010 |
| JP | 49-21022 B | 7/1974 |
| JP | 54-2235 A | 1/1979 |
| JP | 59-196804 A | 11/1984 |
| JP | 63-194799 A | 8/1988 |
| JP | 5-277491 A | 10/1993 |
| JP | 10-511431 A | 11/1998 |
| JP | 2002-509858 A | 4/2002 |
| JP | 2002323741 A | 11/2002 |
| JP | 2002-543294 A | 12/2002 |
| JP | 2002-544199 A | 12/2002 |
| JP | 2004-532351 A | 10/2004 |
| JP | 2006-079093 A | 3/2006 |
| JP | 2011-214064 A | 10/2011 |
| JP | 2012-201966 A | 10/2012 |
| JP | 2013-507446 A | 3/2013 |
| KR | 10-2013-0011943 A | 1/2013 |
| KR | 20140020432 A | 2/2014 |
| TW | 349130 B | 1/1999 |
| WO | WO 90/10732 A1 | 9/1990 |
| WO | WO 96/20295 A1 | 7/1996 |
| WO | WO 96/29449 A1 | 9/1996 |
| WO | WO 97/39610 A1 | 10/1997 |
| WO | WO 99/33824 A1 | 7/1999 |
| WO | WO 00/66810 A1 | 11/2000 |
| WO | WO 02/00965 A1 | 1/2002 |
| WO | WO 02/10326 A1 | 2/2002 |
| WO | WO 02/79105 A1 | 10/2002 |
| WO | WO 2010/048139 A2 | 4/2010 |
| WO | WO 2010/048139 A3 | 4/2010 |
| WO | WO 2011/046954 A1 | 4/2011 |
| WO | WO 2013/076509 A1 | 5/2013 |
| WO | WO 2013/138278 A1 | 9/2013 |

OTHER PUBLICATIONS

Khimiko, "Synthesis and Cytotoxic Activity of 5(6)-Amino-2-[5'(6')-Benzimidazolyl] Benzimadazoles," *Farmatsevticheskii Zhurnal*, 24(1): 31-33 (1990).

Khimmi, "Derivatives of 5(6)-Amino-Benzimidazole," *J. of Organic Chemistry*, 23(3): 637-642 (1987).

Chinese Patent Office, Office Action in Chinese Patent Application No. 201680030844.8, 8 pp. (dated Jul. 30, 2020).

Ashry et al., "Corrosion inhibitors part V: QSAR of benzimidazole and 2-substituted derivatives as corrosion inhibitors by using the quantum chemical parameters," *Progress in Organic Coatings*, NL, 61(1), 11-20 (Oct. 17, 2007).

Ghanbari et al., "Corrosion inhibition performance of three imidazole derivatives on mild steel in 1M phosphoric acid," *Materials Chemistry and Physics*, 124(2-3), 1205-1209 (Dec. 1, 2010).

Zhang et al., "QSAR study on N containing corrosion inhibitors: Quantum chemical approach assisted by topological index," *J. of Mol. Structure (Theochem)*, 732(1-3), 173-182 (Nov. 1, 2005).

European Patent Office, Office Action in European Patent Application No. 16800792.0, 7 pp. (dated Apr. 30, 2020).

Japan Patent Office, Office Action in Japanese Patent Application No. 2017-560983, 2 pp. (dated Jan. 7, 2020).

Japan Patent Office, Office Action in Japanese Patent Application No. 2017-561281, 2 pp. (dated Jun. 30, 2020).

Japan Patent Office, Office Action in Japanese Patent Application No. 2017-561663, 3 pp. (dated Feb. 25, 2020).

(56) References Cited

OTHER PUBLICATIONS

Japan Patent Office, Office Action in Japanese Patent Application No. 2017-561692, 2 pp. (dated Jun. 16, 2020).
Antonijevic et al., "Copper Corrosion Inhibitors. A review," *Int. J. Electrochem. Sci.*,3, 2008, pp. 1-28.
Attayibat, et al., "Quantum chemical studies on N-donors based-pyrazole compounds as corrosion inhibitors for steel in acidic media," *Asian J. Chem* , 21(1), 2009, pp. 105-112.
Bouklah et al., "Pyridine-pyrazole compound as inhibitor for steel in 1 M HCI," *Applied Surface Science*, 240(1-4), Feb. 15, 2015, pp. 341-348.
Brubaker, Jr., "Metal Tetrazole Complexes: Bis-(5-aminotetrazolato)-copper(II)," Kedzie Chemical Laboratory, Michigan State University and Laboratorio De Fisica Nuclear Universidad De Chile, 82, Jun. 5, 1959, pp. 82-85.
Eddy et al., "Theoretical and experimental studies on the corrosion inhibition potentials of some purines for aluminum in 0.1 M HCI," *J. of Adv. Research*, 6(2), Jan. 20, 2014, pp. 203-217.
Finšgar et al., "Inhibition of copper corrosion by 1,2,3-benzotriazole: A review," *Corrosion Science*, 52, 2010, pp. 2737-2749.
Huynh, "The Inhibition of Copper Corrosion in Aqueous Environments With Heterocyclic Compounds," Queensland University of Technology—School of Physical Sciences, Doctorof Philosophy Thesis Examination, 99 pp. (Feb. 2004).
Khaled, "The inhibition of benzimidazole derivatives on corrosion of iron in 1 M HCI solutions," *Electrochimica Acta*, vol. 48, pp. 2493-2503 (2003).
Khaled et al., "Piperidines as corrosion inhibitors for iron in hydrochloric acid," *Journal of Applied Electrochemistry*, 34, 2004, pp. 697-704.
Khaled, "Studies of iron corrosion inhibition using chemical, electrochemical and computer simulation techniques," *Electrochimica Acta*, 55(22), Jun. 17, 2010, pp. 6523-6532.
Korean Intellectual Property Office, International Search Report in International Patent Application No. PCT/US2016/034629, dated Aug. 18, 2016, 4 pp.
Korean Intellectual Property Office, Written Opinion in International Patent Application No. PCT/US2016/034629, dated Aug. 18, 2016, 8 pp.
Lewis, "The Corrosion Inhibition of Copper by Benzimidazole," *Corrosion Science*, vol. 22, No. 6, pp. 579-584 (1982).
Li et al., "Synergistic inhibition effect of 6-benzylaminopurine and iodide ion on the corrosion of cold rolled steel in $H_3PO_4$ solution," *Corrosion Science*, 53(11), Nov. 2011, pp. 3704-3711.
Liu et al., "Electromechanical and Quantum Chemical Studies of 5-Substituted Tetrazoles as Corrosion Inhibitors for Copper in Aerated 0.5 M $H_2SO_4$ Solution," *Materials Sciences and Applications*, 2, 2011, pp. 1268-1278.
Maji et al., "Corrosion inhibition of brass in presence of sulphonamidoimidazoline and hydropyrimidine in chloride solution," *Indian Journal of Chemical Technology*, vol. 16, pp. 221-227 (May 2009).
Nalco Chemical Company, Analytical Report, "Inhibitor AZ8104," Oct. 19, 1999, 6 pp.
Nalco Chemical Company, Analytical Report, "Inhibitor AZ8104," Oct. 5, 1999, 2 pp.
Nalco Chemical Company, Analytical Report, "10% As NaCITT—Research," Oct. 19, 1999, 6 pp.
Obot et al., "Benzimidazole: Small planar molecule with diverse anti-corrosion potentials," *Journal of Molecular Liquids*, vol. 246, pp. 66-90 (2017).
Oliphant, "Causes of Copper Corrosion in Plumbing Systems," A Review of Current Knowledge, FR/R0007, Sep. 2010, Foundation for Water Research, Bucks, U.K., 35 pp.
Pillard et al., "Toxicity of Benzotriazole and Benzotriazole Derivatives to Three Aquatic Species," *Wat. Res.* 35(2), 2001, pp. 557-560.
Ravichandran et al., "Corrosion inhibition of brass by benzotriazole derivatives in NaCl solution," *Anti-Corrosion Methods and Materials*, 52(4), 2005, pp. 226-232.

Scendo, "Corrosion inhibition of copper by purine or adenine in sulphate solutions," *Corrosion Science*, 49(10), Oct. 2007, pp. 3953-3968.
Scendo et al., "Adenine as an Effective Corrosion Inhibitor for Stainless Steel in Chloride Solution" *Int. J. Electrochem. Sci.*, 8, 2013, pp. 9201-9221.
Sherif, "Electrochemical and Gravimetric Study on the Corrosion and Corrosion Inhibition of Pure Copper in Sodium Chloride Solutions by Two Azole Derivatives," *Int. J. Electrochem. Sci.*, 7, 2012, pp. 1482-1495.
Shreir, "Effects of Inhibitors on Corrosion Processes," *Corrosion*, vol. 2—Corrosion Control, Newnes-Butterworths, London, England, pp. 18:38 and 18:41 (1976).
Solehudin, "Performance of Benzotriazole as Corrosion Inhibitors of Carbon Steel in Chloride Solution Containing Hydrogen Sulfide," *International Refereed Journal of Engineering and Science*, 1(4), Dec. 2012, pp. 21-26.
Su et al., "Corrosion Inhibition Performance of Benzimidazole N-Mannich Base for Mild Steel in Hydrochloric Acid," *Journal of Chinese Society for Corrosion and Protection*, vol. 35, No. 5, pp. 415-422 (Oct. 2015).
Téllez et al., "Coordination behavior of benzimidazole, 2-substituted benzimidazoles and benzothiazoles, towards transition metal ions," *ARKIVOC*, Issue in Honor of Prof. Rosalinda Contreras Theurel, ISSN 1551-7012, 2008, pp. 245-275.
Yanardag et al., "Corrosion Inhibition Efficiency of Benzimidazole and Benzimidazole Derivatives for Zinc, Copper and Brass," *Asian Journal of Chemistry*, vol. 24, No. 1, pp. 47-52 (2012).
Zhang et al., "Performance and theoretical study on corrosion inhibition of 2-(4-pyridyl)-benzimidazole for mild steel in hydrochloric acid," *Corrosion Science*, 61, Apr. 3, 2012, pp. 1-9.
U.S. Appl. No. 15/166,527, filed May 27, 2016.
Chinese Patent Office, Search Report in Chinese Patent Application No. 201680030883.8, 2 pp. (dated Nov. 7, 2019).
Cruz-Gonzalez et al., "Adenine and guanine derivative bases of purines and their corresponding nucleosides as corrosion inhibitors in 1M hydrochloric acid," *ECS Transactions*, 36.1: 179-185 (2011).
European Patent Office, Partial Supplementary European Search Report in European Patent Application No. 16800794.6, 8 pp. (dated Oct. 18, 2018).
European Patent Office, Extended European Search Report in European Patent Application No. 16800789.6, 7 pp. (dated Nov. 29, 2018).
European Patent Office, Extended European Search Report in European Patent Application No. 16800792.0, 11 pp. (dated Dec. 4, 2018).
European Patent Office, Extended European Search Report in European Patent Application No. 16800794.6, 8 pp. (dated Jan. 29, 2019).
European Patent Office, Extended European Search Report in European Patent Application No. 16800796.1, 14 pp. (dated Mar. 13, 2019).
Korean Intellectual Property Office, International Search Report in International Patent Application No. PCT/US2016/034641, dated Oct. 4, 2016, 4 pp.
Korean Intellectual Property Office, Written Opinion in International Patent Application No. PCT/US2016/034641, dated Oct. 4, 2016, 10 pp.
Korean Intellectual Property Office, International Search Report in International Patent Application No. PCT/US2016/034635, dated Oct. 6, 2016, 4 pp.
Korean Intellectual Property Office, Written Opinion in International Patent Application No. PCT/US2016/034635, dated Oct. 6, 2016, 8 pp.
Korean Intellectual Property Office, International Search Report in International Patent Application No. PCT/US2016/034619, dated Apr. 11, 2017, 4 pp.
Korean Intellectual Property Office, Written Opinion in International Patent Application No. PCT/US2016/034619, dated Apr. 11, 2017, 6 pp.

(56) References Cited

OTHER PUBLICATIONS

Rehim et al., "On the corrosion inhibition of low carbon steel in concentrated sulphuric acid solutions. Part I: Chemical and electrochemical (AC and DC) studies," *Corrosion Science*, 50: 2258-2271 (2008).
Scendo, "Purine and Adenine as Corrosion Inhibitors for Copper in Acidic Chloride Solutions," Mieczyslaw; Wydawnictwo Sigma-Not (2007).
Scendo, "The Influence of Adenine on Corrosion of Copper in Chloride Solutions," *Corrosion Science*, 50(7): 2070-2077 (2008).

* cited by examiner

2-SUBSTITUTED IMIDAZOLE AND BENZIMIDAZOLE CORROSION INHIBITORS

CROSS-REFERENCE TO RELATED APPLICATION

This patent application is a continuation of copending U.S. patent application Ser. No. 15/166,527, filed May 27, 2016, which claims priority to U.S. Provisional Patent Application No. 62/167,697, filed May 28, 2015, all of which preceding applications are incorporated in their entireties herein by reference.

FIELD OF INVENTION

The invention relates to methods of using heterocyclic compounds as corrosion inhibitors for metal surfaces in aqueous environments.

BACKGROUND OF THE INVENTION

Copper and copper alloy components are commonly used in industrial systems due to copper's high thermal conductivity and anti-microbial properties. Copper and copper alloys (e.g., bronze and brass) are relatively resistant to corrosion as a result of protective film layers that naturally coat the surface of copper, which include an inner cuprous oxide film layer and an outer cupric oxide film layer. Under anaerobic conditions, these protective layers generally reduce the rate of further corrosion of the metal surface. However, under certain conditions, copper and copper alloys are susceptible to corrosion. In the presence of oxygen and under acidic conditions, oxidation of copper and dissolution of the copper (II) ion into water can occur.

Copper corrosion inhibitors are commonly added to industrial water systems to prevent and reduce dissolution of copper from system surfaces. In particular, the use of nitrogen-containing compounds such as azoles is well known for inhibiting the corrosion of copper and copper alloys. It is generally believed that the nitrogen lone pair electrons coordinate to the metal, resulting in the formation of a thin organic film layer that protects the copper surface from elements present in the aqueous system. Nitrogen-containing compounds such as azoles are also known to precipitate copper (II) from the aqueous solution, hindering corrosion that can occur due to galvanic reactions between copper and other metals.

Oxidizing halogens are commonly used as biocides in industrial systems to control slime and microbiological growth in water. The protective film provided by many azoles erodes in the presence of oxidizing halogens such as chlorine, hypochlorite, and hypobromite, reducing the effectiveness of the corrosion inhibitor. Moreover, a decrease in copper (II) precipitation often occurs in the presence of oxidizing halogens due to halogen attack of the corrosion inhibitor in solution. Thus, in the presence of oxidizing halogens, an excess or continuous injection of corrosion inhibitor is often required to maintain the organic protective film.

It would be desirable to provide a method of using a corrosion inhibitor that provides protection of copper in the absence and presence of oxidizing halogen agents.

BRIEF SUMMARY OF THE INVENTION

In an embodiment, the invention provides a method for inhibiting corrosion of a metal surface in contact with an aqueous system. The method comprises adding to the aqueous system a compound of formula (I),

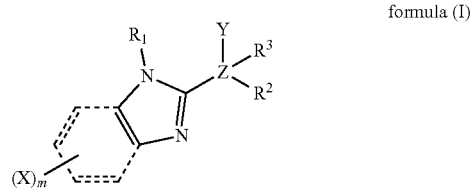

formula (I)

wherein each X is the same or different, and is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl;

Y is selected from the group consisting of hydroxyl, halogen, oxo, alkoxy, thiol, alkylthio, amino, hydrogen, and aminoalkyl;

Z is selected from the group consisting of carbon and nitrogen;

$R^1$ is selected from the group consisting of hydrogen, deuterium, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, hydroxyl, and carbonyl;

$R^2$ are $R^3$ are selected from the group consisting of hydrogen, halogen, hydroxyl, aryl, phenyl, heteroaryl, benzyl, alkylheteroaryl, carbonyl, $C_2$-$C_{16}$ alkenyl, $C_2$-$C_{16}$ alkynyl, $C_3$-$C_8$ cycloalkyl, and $C_1$-$C_{16}$ alkyl; and m is 1, 2, 3, or 4; or a salt thereof.

In another embodiment, the invention provides a method for inhibiting corrosion of a metal surface in contact with an aqueous system comprising an oxidizing halogen compound. The method comprises adding to the aqueous system a compound of formula (II),

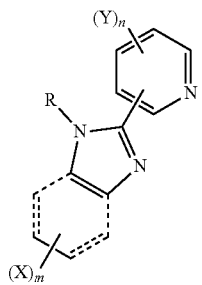

formula (II)

wherein each of X and Y is the same or different, and is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl;

R is selected from the group consisting of hydrogen, deuterium, $C_1$-$C_{16}$ alkyl, aryl, $C_2$-$C_{16}$ alkenyl, $C_2$-$C_{16}$ alkynyl, heteroaryl, $C_3$-$C_5$ cycloalkyl, benzyl, alkylheteroaryl, halogen, hydroxyl, and carbonyl;

m is 1, 2, 3, or 4; and n is 1, 2, 3, or 4; or a salt thereof.

In another embodiment, the invention provides a formulation for inhibiting corrosion of a metal surface in contact with an aqueous system. The formulation comprises a compound of formula (I) or (II), a phosphoric acid, and a phosphinosuccinic oligomer.

DETAILED DESCRIPTION OF THE INVENTION

Figure 1:
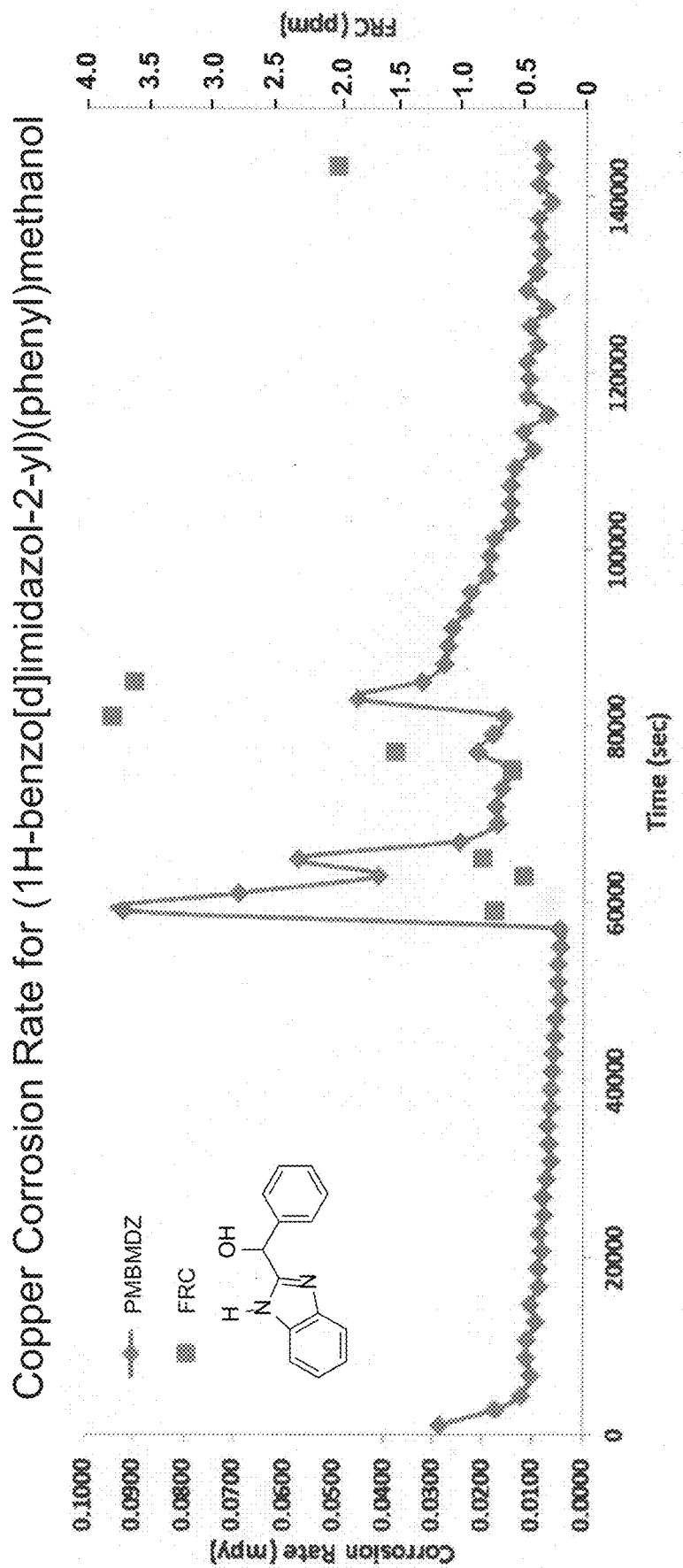
FIG. 1 is a line graph that illustrates the corrosion rate of copper using (1H-benzo[d]imidazol-2-yl)(phenyl)methanol as a corrosion inhibitor in the absence and presence of bleach.

The following definitions are provided to determine how terms used in this application, and in particular, how the claims are to be construed. The organization of the definitions is for convenience only and is not intended to limit any of the definitions to any particular category.

"Alkoxy" refers to a moiety of the formula RO—, where R is alkyl, alkenyl, or alkynyl;

"Alkyl" refers to a straight-chain or branched alkyl substituent. Examples of such substituents include methyl, ethyl, propyl, isopropyl, n-butyl, sec-butyl, isobutyl, tert-butyl, pentyl, isoamyl, hexyl, and the like;

"Alkylheteroaryl" refers to an alkyl group linked to a heteroaryl group;

"Alkenyl" refers to a straight or branched hydrocarbon, preferably having 2, 3, 4, 5, 6, 7, 8, 9, 10, 11, 12, 13, 14, 15, or 16 carbons, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl. Alkenyl groups may be unsubstituted or substituted by one or more suitable substituents;

"Alkylthio" refers to a moiety of the formula RS—, where R is alkyl, aryl, alkenyl, or alkynyl;

"Alkynyl" refers to a straight or branched hydrocarbon, preferably having 2, 3, 4, 5, 6, 7, 8, 9, 10, 11, 12, 13, 14, 15, or 16 carbons, and having one or more carbon-carbon triple bonds. Alkynyl groups include, but are not limited to, ethynyl, propynyl, and butynyl. Alkynyl groups may be unsubstituted or substituted by one or more suitable substituents;

"Amino" refers to the moiety $H_2N$—;

"Aminoalkyl" refers to a nitrogen substituent attached to one or more carbon groups, such as alkyl or aryl. For example, the aminoalkyl group can be RHN— (secondary) or $R_2N$— (tertiary) where R is alkyl or aryl;

"Aqueous system" refers to any system containing metal components which are in contact with water on a periodic or continuous basis;

"Aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2n electrons, according to Hückel's Rule;

"Carbonyl" refers to a substituent comprising a carbon double bonded to an oxygen. Examples of such substituents include aldehydes, ketones, carboxylic acids, esters, amides, and carbamates;

"Cycloalkyl" refers to a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with alkyl groups such as methyl groups, ethyl groups, and the like;

"Halogen" or "halo" refers to F, Cl, Br, and I;

"Halosubstituted alkyl" refers to an alkyl group as described above substituted with one or more halogens, for example, chloromethyl, trifluoromethyl, 2,2,2-trichloroethyl, and the like;

"Heteroaryl" refers to a monocyclic or bicyclic 5- or 6-membered ring system, wherein the heteroaryl group is unsaturated and satisfies Hückel's rule. Non-limiting examples of heteroaryl groups include furanyl, thiophenyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, triazinyl, benzofuranyl, benzothiophenyl, indolyl, quinolinyl, isoquinolinyl, benzimidazolyl, benzoxazolinyl, benzothiazolinyl, quinazolinyl, and the like;

"Industrial water system" means any system that circulates water as its primary ingredient. Nonlimiting examples of "industrial water systems" include cooling systems, boiler systems, heating systems, membrane systems, paper making process or any other system that circulates water as defined below;

"Mild steel" refers to carbon and low alloy steels;

"Oxo" refers to an oxygen atom double-bonded to a carbon atom;

"Oxidizing halogen" refers to an oxidizing agent comprising at least one halogen. Examples of oxidizing halogens include, but are not limited to, chlorine bleach, chlorine, bromine, iodine, hypochlorite, hypobromite, iodine/hypoiodous acid, hypobromous acid, halogenated hydantoins, chlorine dioxide, stabilized versions of hypochlorous or hypobromous acids, and compounds or chemical groups capable of releasing chlorine, bromine, or iodine;

"Water" means any substance that has water as a primary ingredient. Water may include pure water, tap water, fresh water, recycled water, brine, steam, and/or any aqueous solution, or aqueous blend.

For convenience of reference herein, the structures of the compounds of formula (I) are numbered as follows:

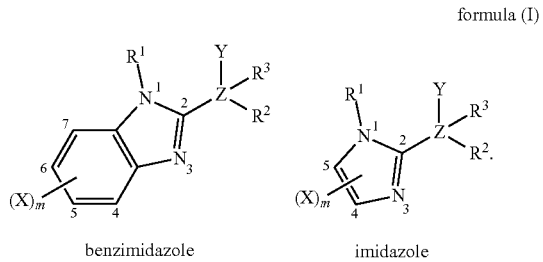

formula (I)

benzimidazole          imidazole

For convenience of reference herein, the structure of the compounds of formula (II) is numbered as follows:

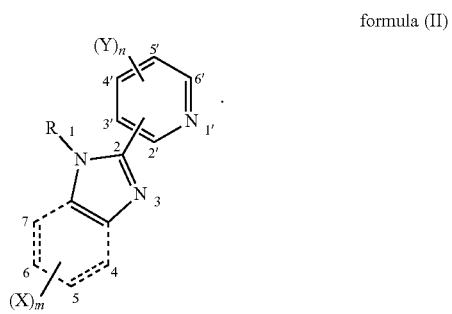

formula (II)

The dotted lines denote that the compounds of formulae (I) and (II) can be a 2-substituted imidazole-based compound or a 2-substituted benzimidazole-based compound.

Whenever a range of the number of atoms in a structure is indicated (e.g., a $C_1$-$C_{16}$ alkyl, $C_2$-$C_{16}$ alkenyl, $C_2$-$C_{16}$ alkynyl, etc.), it is specifically contemplated that any sub-range or individual number of carbon atoms falling within the indicated range also can be used. Thus, for instance, the recitation of a range of 1-16 carbon atoms (e.g., $C_1$-$C_{16}$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-16 carbon atoms (e.g., $C_2$-$C_{16}$) as used with respect to any chemical group (e.g., alkyl) referenced herein encompasses and specifically describes 1, 2, 3, 4, 5, 6, 7, 8, 9, 10, 11, 12, 13, 14, 15, and/or 16 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 1-13 carbon atoms, 1-14 carbon atoms, 1-15 carbon atoms, 1-16 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 2-13 carbon atoms, 2-14 carbon atoms, 2-15 carbon atoms, 2-16 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 3-13 carbon atoms, 3-14 carbon atoms, 3-15 carbon atoms, 3-16 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, 4-12 carbon atoms, 4-13 carbon atoms, 4-14 carbon atoms, 4-15 carbon atoms, and/or 4-16 carbon atoms, etc., as appropriate).

The invention provides methods of using heterocyclic compounds and formulations comprising heterocyclic compounds that are particularly useful for inhibiting corrosion of metallic components in industrial water systems. Applicants have surprisingly and unexpectedly discovered that a method comprising adding to an aqueous system an imidazole or a benzimidazole capable of undergoing chelation with a metal provides excellent metal corrosion resistance. In particular, Applicants have discovered that adding imidazoles or benzimidazoles substituted with a 2-pyridyl or a benzyl alcohol to an aqueous system in contact with a metal surface leads to excellent corrosion inhibition for metals such as copper. Moreover, while benzotriazoles and benzimidazoles are generally unstable in the presence of oxidizing halogen compounds, Applicants have discovered that imidazoles and benzimidazoles capable of undergoing 1,2-chelation with a metal impart exemplary protection of metal in the presence of oxidizing halogen compounds. In particular, 2-(2-pyridyl)benzimidazoles and 1H-benzo[d]imidazol-2-yl)(phenyl)methanols provide greater protection against corrosion than benzimidazole, 2-phenylbenzimidazole, and tolyltriazole in the presence of oxidizing halogen compounds. While not wishing to be bound by any particular theory, it is believed that the methods of the present invention provide a protective film that is essentially impenetrable by common oxidizing halogen compounds due to bidentate chelation of the corrosion inhibitor with the metal surface. Thus, in certain embodiments, the methods of the present invention provide protection against metal corrosion in aqueous systems which employ oxidizing halogen compounds as biocides.

In an embodiment, the invention provides a method for inhibiting corrosion of a metal surface in contact with an aqueous system. The method comprises adding to the aqueous system a compound of formula (I),

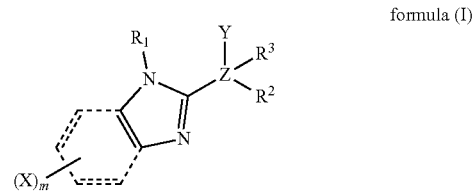

formula (I)

wherein each X is the same or different, and is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl;

Y is selected from the group consisting of hydroxyl, halogen, oxo, alkoxy, thiol, alkylthio, amino, hydrogen, and aminoalkyl;

Z is selected from the group consisting of C and nitrogen;

$R^1$ is selected from the group consisting of hydrogen, deuterium, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, hydroxyl, and carbonyl;

$R^2$ and $R^3$ are selected from the group consisting of hydrogen, halogen, hydroxyl, aryl, phenyl, heteroaryl, benzyl, alkylheteroaryl, carbonyl, $C_2$-$C_{16}$ alkenyl, $C_2$-$C_{16}$ alkynyl, $C_3$-$C_8$ cycloalkyl, and $C_1$-$C_{16}$ alkyl; and m is 1, 2, 3, or 4; or a salt thereof.

The X substituent or substituents as shown can occupy any available position on the imidazole or benzimidazole ring. Thus, in certain embodiments, the X substituent or substituents can be located at the 4-position, 5-position, 6-position, and/or 7-position of the benzimidazole. In certain preferred embodiments, the X substituent is at the 5-position. The X substituent or substituents as shown can occupy any available position on the imidazole ring. Thus, in certain embodiments, the X substituent or substituents can be located at the 4-position and/or 5-position of the imidazole.

As disclosed above, m can be 1, 2, 3, or 4. If m is 2, 3, or 4, the X substituents can occupy any open position and can be positioned ortho-, meta-, or para- to each other.

In certain embodiments, the compound of formula (I) is an imidazole.

In certain embodiments, the compound of formula (I) is a benzimidazole.

In certain preferred embodiments, X is electron-rich or a $C_1$-$C_{16}$ alkyl group.

In certain preferred embodiments, X is hydrogen.

In certain preferred embodiments, X is $C_1$-$C_{16}$ alkyl.

In certain preferred embodiments, X is methyl.

In certain preferred embodiments, Y is hydroxyl.

In certain preferred embodiments, $R^1$ is hydrogen.

In certain preferred embodiments, $R^2$ is aryl or heteroaryl.

In certain preferred embodiments, $R^2$ is phenyl.

In certain preferred embodiments, Y is not present when Z is nitrogen.

In certain preferred embodiments, the compound of formula (I) is

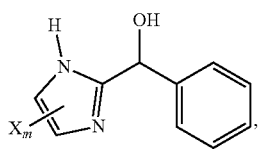

wherein $X_m$ is the same as disclosed above.

In certain preferred embodiments, the compound of formula (I) is

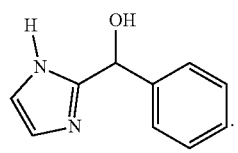 [SMILES: OC(c1ccccc1)c1ncc[nH]1]

In certain preferred embodiments, the compound of formula (I) is

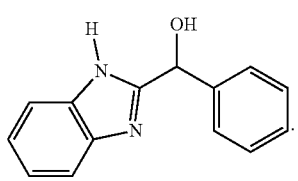 [SMILES: OC(c1ccccc1)c1nc2ccccc2[nH]1]

In certain preferred embodiments, the compound of formula (I) is

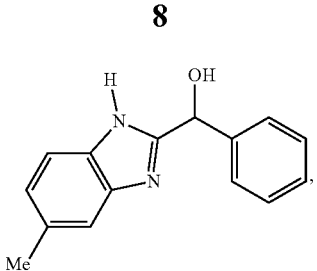

wherein Me is methyl.

In certain embodiments, the compound of formula (I) is

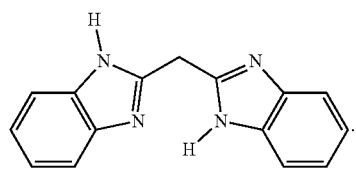 [SMILES: c1ccc2[nH]c(Cc3nc4ccccc4[nH]3)nc2c1]

In certain embodiments, the compound of formula (I) is

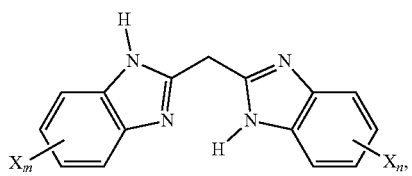

where each X is the same or different and m and n are 1, 2, 3, or 4.

In certain preferred embodiments, the compound of formula (I) is

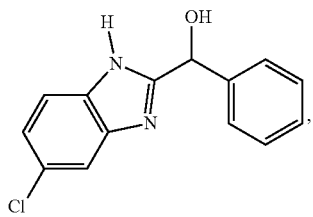

wherein Cl is chlorine.

In certain preferred embodiments, the compound of formula (I) is

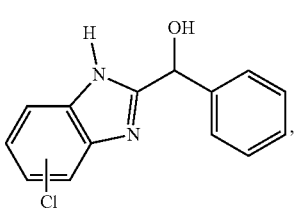

wherein Cl is chlorine.

In certain preferred embodiments, the compound of formula (I) is

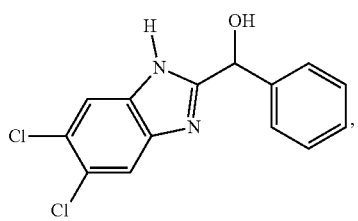

wherein Cl is chlorine.

In certain preferred embodiments, the compound of formula (I) is

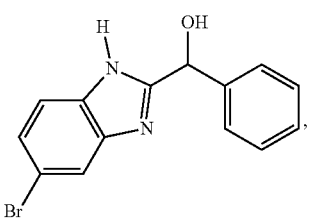

wherein Br is bromine.

In certain preferred embodiments, the compound of formula (I) is

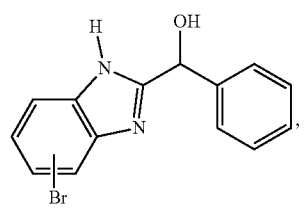

wherein Br is bromine.

In certain preferred embodiments, the compound of formula (I) is

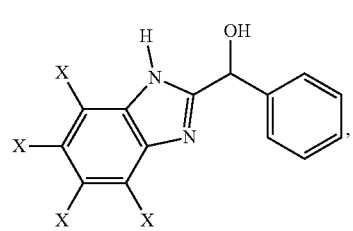

wherein X is chlorine or bromine.

In certain preferred embodiments, the compound of formula (I) is

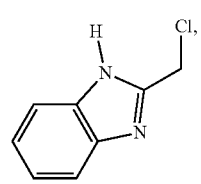

wherein Cl is chlorine.

In certain preferred embodiments, the compound of formula (I) is

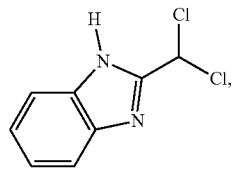

wherein Cl is chlorine.

In certain preferred embodiments, the compound of formula (I) is

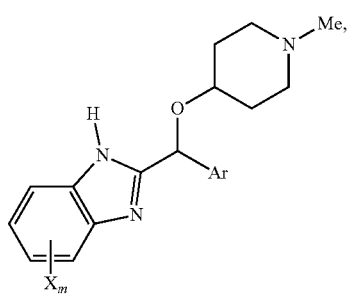

where Ar is aryl and Me is methyl.

In certain embodiments, the compound of formula (I) is

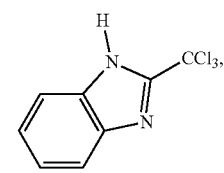

wherein Cl is chlorine.

In certain embodiments, the compound of formula (I) is

wherein Me is methyl.

In certain embodiments, the compound of formula (I) is

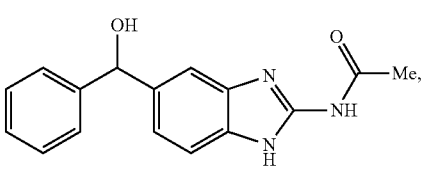

wherein Me is methyl.

In certain embodiments, the compound of formula (I) is a chloride salt, bromide salt, iodide salt, sulfate salt, fluoride salt, perchlorate salt, acetate salt, trifluoroacetate salt, phosphate salt, nitrate salt, carbonate salt, bicarbonate salt, formate salt, chlorate salt, bromated salt, chlorite salt, thiosulfate salt, oxalate salt, cyanide salt, cyanate salt, tetrafluoroborate salt, and the like. In certain preferred embodiments, the compound of formula (I) is hydrochloride or sulfate salt.

In certain preferred embodiments, $R^1$ is hydrogen. While not wishing to be bound by any particular theory, it is postulated that when $R^1$ is hydrogen, hydrogen-bonding can occur between molecules when added to an aqueous system in contact with a metal surface, thereby resulting in enhanced strength of the corrosion inhibitor protective film on the metal surface. Moreover, compounds of formula (I) where $R^1$ is hydrogen generally have increased water solubility.

In certain preferred embodiments, X is an electron-rich group or an alkyl group. While not wishing to be bound by any particular theory, it is postulated that when X is more electron-rich, the nitrogen atoms in the imidazole ring may have increased electron density. It is believed that nitrogen atoms having a greater electron density will have stronger coordination with the metal surface of the aqueous system, resulting in a stronger protective film. However, in certain embodiments, X is electron-deficient.

The compounds of formula (I) can be a single enantiomer (i.e., (R)-isomer or (S)-isomer), a racemate, or a mixture of enantiomers at any ratio.

The compounds of formula (I) can be prepared by any suitable synthetic chemical method. One method of preparation is a one-step synthesis using commercially available materials. At elevated temperature, a 1,2-phenylenediamine undergoes a condensation reaction with an appropriate carboxylic acid in the presence of an acid. For example, mandelic acid reacts with 4-methyl-o-phenylenediamine in the presence of hydrochloric acid to form (5-methyl-1H-benzo[d]imidazol-2-yl)(phenyl)methanol. Any suitable Lewis or Brönsted acid can be used in the synthesis including, but not limited to, hydrochloric acid, polyphosphoric acid, Eaton's reagent, sulfuric acid, p-toluenesulfonic acid, and triflic acid. In certain preferred embodiments, hydrochloric acid is used.

In another embodiment, the invention provides a method for inhibiting corrosion of a metal surface in contact with an aqueous system comprising an oxidizing halogen compound, the method comprising adding to the aqueous system a compound of formula (II),

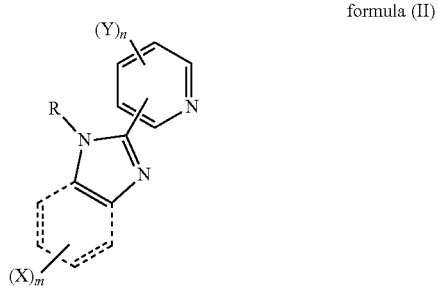

formula (II)

wherein each of X and Y is the same or different, and is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl;

R is selected from the group consisting of hydrogen, deuterium, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, hydroxyl, and carbonyl;

m is 1, 2, 3, or 4; and n is 1, 2, 3, or 4; or a salt thereof.

The X substituent or substituents as shown can occupy any available position on the benzimidazole ring. Thus, in certain embodiments, the X substituent or substituents can be located at the 4-position, 5-position, 6-position, and/or 7-position of the benzimidazole. In certain preferred embodiments, the X substituent is at the 5-position. The X substituent or substituents as shown can occupy any available position on the imidazole ring. Thus, in certain embodiments, the X substituent or substituents can be located at the 4-position and/or 5-position of the imidazole.

The Y substituent or substituents as shown can occupy any available position on the pyridyl ring. Thus, in certain embodiments, the Y substituent or substituents can be located at the 2'-position, 3'-position, 4'-position, 5'-position, and/or 6'-position of the pyridyl ring.

As disclosed above, m can be 1, 2, 3, or 4. If m is 2, 3, or 4, the X substituents can occupy any open position and can be positioned ortho-, meta-, or para- to each other.

As disclosed above, n can be 1, 2, 3, or 4. If n is 2, 3, or 4, the Y substituents can occupy any open position and can be positioned ortho-, meta-, or para- to each other.

In certain preferred embodiments, X and Y are individually chosen electron-rich or a $C_1$-$C_{16}$ alkyl group.

In certain preferred embodiments, R is hydrogen.

In certain preferred embodiments, X is $C_1$-$C_{16}$ alkyl and Y is hydrogen.

In certain preferred embodiments, X and Y are hydrogen.

In certain preferred embodiments, X is methyl, Y is hydrogen, m is 1, and n is 1.

In certain preferred embodiments, the imidazole or benzimidazole is located at the 2'-position of the pyridyl ring.

In certain preferred embodiments, the compound of formula (II) is

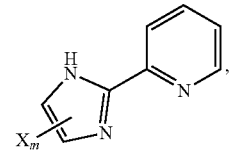

wherein $X_m$ is the same as disclosed above.

In certain preferred embodiments, the compound of formula (II) is

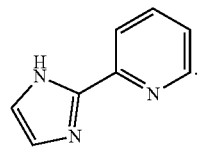 [SMILES: c1ccc(-c2ncc[nH]2)nc1]

In certain preferred embodiments, the compound of formula (II) is

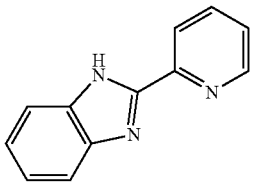

In certain preferred embodiments, the compound of formula (II) is

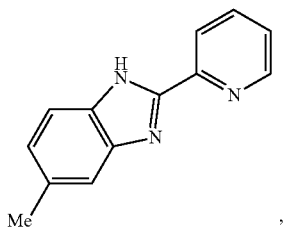

wherein Me is methyl.

In certain preferred embodiments, the compound of formula (II) is

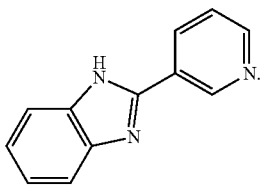 [SMILES: c1cncc(-c2nc3ccccc3[nH]2)c1]

In certain preferred embodiments, the compound of formula (II) is

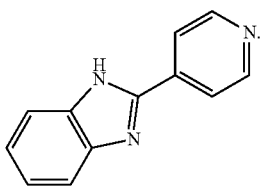 [SMILES: c1ccc2[nH]c(-c3ccncc3)nc2c1]

In certain embodiments, a compound of formula (II) is a chloride salt, bromide salt, iodide salt, sulfate salt, fluoride salt, perchlorate salt, acetate salt, trifluoroacetate salt, phosphate salt, nitrate salt, carbonate salt, bicarbonate salt, formate salt, chlorate salt, bromated salt, chlorite salt, thiosulfate salt, oxalate salt, cyanide salt, cyanate salt, tetrafluoroborate salt, and the like. In certain preferred embodiments, a compound of formula (II) is a hydrochloride or sulfate salt.

In certain preferred embodiments, R is hydrogen. While not wishing to be bound by any particular theory, it is postulated that when R is hydrogen, hydrogen-bonding can occur between molecules when added to an aqueous system in contact with a metal surface, thereby resulting in enhanced strength of the corrosion inhibitor protective film on the metal surface. Moreover, compounds of formula (II) where R is hydrogen generally have increased water solubility.

In certain preferred embodiments, X and/or Y is an electron-rich group or an alkyl group. While not wishing to be bound by any particular theory, it is postulated that when X or Y is more electron-rich, the nitrogen atoms in the imidazole ring may have increased electron density. It is believed that nitrogen atoms having a greater electron density will have stronger coordination with the metal surface of the aqueous system, resulting in a stronger protective film. However, in certain embodiments, X and/or Y is electron-deficient.

The compounds of formula (II) can be prepared by any suitable synthetic chemical method. One method of preparation is a one-step synthesis using commercially available materials. At elevated temperature, a 1,2-phenylenediamine undergoes a condensation reaction with a pyridyl carboxylic acid (e.g., picolinic acid) in the presence of an acid. For example, 2-picolinic acid reacts with o-phenylenediamine in the presence of polyphosphoric acid to form 2-(2-pyridyl)benzimidazole. Any suitable Lewis or Brönsted acid can be used in the synthesis including, but not limited to, polyphosphoric acid, Eaton's Reagent, hydrochloric acid, sulfuric acid, p-toluenesulfonic acid, and triflic acid. In certain preferred embodiments, polyphosphoric acid is used.

As disclosed above, in certain preferred embodiments, the imidazole or benzimidazole is located at the 2'-position of the pyridyl ring. Applicants have discovered that a method comprising adding 2-(2-pyridyl)benzimidazoles to an aqueous system in contact with a metal provides enhances corrosion resistance in the presence of oxidizing halogen compounds. While 2-(2-pyridyl)benzimidazole, 2-(3-pyridyl)benzimidazole, and 2-(4-pyridyl)benzimidazole provide excellent corrosion resistance, it was surprisingly and unexpectedly discovered that 2-(2-pyridyl)benzimidazole maintains a comparable corrosion resistance in the absence and presence of an oxidizing halogen compound. While not wishing to be bound by any particular theory, it is postulated that 2-(2-pyridyl)benzimidazoles are capable of forming a stable 1,2-chelation complex with the metal surface. The 3-pyridyl and 4-pyridylbenzimidazole compounds are incapable of forming a 1,2-chelation complex, resulting in an organic film having lower stability in the presence of oxidizing halogen compounds.

The compounds of formulae (I) and (II) may provide corrosion protection for any metal or metal alloy including, but not limited to, copper, iron, silver, steel (e.g., galvanized steel), and aluminum. In certain preferred embodiments, a compound of formula (I) or (II) is added to an aqueous system in contact with a metal surface comprising copper to inhibit metal corrosion. In certain preferred embodiments, a compound of formula (I) or (II) is added to an aqueous system in contact with a metal surface comprising a copper alloy to inhibit metal corrosion. In certain embodiments, copper complexes with one or more heteroatoms in a compound of formula (I) or (II). In certain embodiments, copper complexes with one or more heteroatoms in a compound of formula (I) or (II). Copper has a wide-range of applications, including use as copper piping and tubing in plumbing and industrial machinery. Copper and copper alloys are well known for their use in cooling water and boiler water systems.

The compounds of formulae (I) and (II) can be used to protect any copper alloy, including bronze and brass. Bronze commonly comprises copper and tin, but may comprise other elements including aluminum, manganese, silicon, arsenic, and phosphorus. Brass comprises copper and zinc, and is commonly used in piping in water boiler systems. In certain embodiments, a compound of formula (I) or (II) is added to an aqueous system in contact with a metal surface comprising bronze to inhibit metal corrosion. In certain preferred embodiments, a compound of formula (I) or (II) is added to an aqueous system in contact with a metal surface comprising brass (e.g., admirality brass) to inhibit metal corrosion. In certain preferred embodiments, a compound of formula (I) or (II) is added to an aqueous system in contact with a metal surface comprising a copper-nickel alloy to inhibit metal corrosion.

In certain embodiments, a compound of formula (I) or (II) inhibits the corrosion of mild steel. In certain embodiments, a compound of formula (I) or (II) inhibits the corrosion of metal alloys including, but not limited to, galvanized steel, stainless steel, cast iron, nickel, and combinations thereof. While not wishing to be bound by any particular theory, it is postulated that the compounds of formulae (I) and (II) inactivate Cu (II) in solution, preventing the occurrence of galvanic cells on the steel surface. Thus, in certain embodiments, a compound of formula (I) or (II) inhibits pitting corrosion of mild steel.

The corrosion rate provided by compounds of formulae (I) and (II) is not limited. In certain embodiments, a compound of formula (I) or (II) provides a metal corrosion rate that is acceptable according to industry standards, e.g., about 0.2 mpy or less. In certain preferred embodiments, a compound of formula (I) or (II) provides a metal corrosion rate of about 0.1 mpy or less. Thus, in certain preferred embodiments, a compound of formula (I) or (II) provides a metal corrosion rate of about 0.1 mpy or less, about 0.05 mpy or less, about 0.04 mpy or less, about 0.03 mpy or less, about 0.02 mpy or less, about 0.01 mpy or less, about 0.005 mpy or less, or about 0.002 mpy or less.

While the compounds of formulae (I) and (II) can be added to an aqueous system at any dosage rate, the compounds of formulae (I) and (II) are generally added to an aqueous system at a dosage rate of from about 0.01 ppm to about 500 ppm. In certain embodiments, a compound of formula (I) or (II) is added to an aqueous system at a dosage rate of from about 0.01 ppm to about 100 ppm. Thus, in certain preferred embodiments, a compound of formula (I) or (II) is added to an aqueous system at a dosage rate of from about 0.01 ppm to about 100 ppm, from about 0.01 ppm to about 75 ppm, from about 0.01 ppm to about 50 ppm, from about 0.01 ppm to about 25 ppm, from about 0.01 ppm to about 10 ppm, from about 0.01 ppm to about 5 ppm, from about 0.1 ppm to about 100 ppm, from about 0.1 ppm to about 75 ppm, from about 0.1 ppm to about 50 ppm, from about 0.1 ppm to about 25 ppm, from about 0.1 ppm to about 10 ppm, from about 0.1 ppm to about 5 ppm, from about 1 ppm to about 100 ppm, from about 1 ppm to about 75 ppm, from about 1 ppm to about 50 ppm, from about 1 ppm to about 25 ppm, from about 1 ppm to about 10 ppm, from about 5 ppm to about 100 ppm, from about 10 ppm to about 100 ppm, from about 25 ppm to about 100 ppm, from about 50 ppm to about 100 ppm, or from about 80 ppm to about 100 ppm.

The compounds of formulae (I) and (II) can be used to inhibit corrosion of metal in an aqueous system having any pH. In certain preferred embodiments, a compound of formula (I) or (II) is added to an aqueous system having a pH of from about 6 to about 12. Thus, in certain preferred embodiments, a compound of formula (I) or (II) is added to an aqueous system having a pH of from about 6 to about 12, from about 6 to about 11, from about 6 to about 10, from about 6 to about 9, from about 6 to about 8, from about 7 to about 12, from about 8 to about 12, from about 9 to about 12, from about 7 to about 10, or from about 8 to about 10.

An advantage of the present methods is that compounds of formulae (I) and (II) generally provide corrosion protection for metal surfaces in the presence of oxidizing halogens. In certain preferred embodiments, a compound of formula (I) or (II) is added to an aqueous system in contact with a metal surface and provides corrosion protection for metal surface in the presence of any oxidizing halogen compound. In certain preferred embodiments, a compound of formula (I) or (II) inhibits metal corrosion in the presence of oxidizing halogen compounds including, but not limited to, hypochlorite bleach, chlorine, bromine, hypochlorite, hypobromite, chlorine dioxide, iodine/hypoiodous acid, hypobromous acid, halogenated hydantoins, stabilized versions of hypochlorous or hypobromous acids, or combinations thereof. While not wishing to be bound by any particular theory, it is postulated that the relatively large number of heteroatoms of the compounds of formulae (I) and (II) provide a greater number of sites for bonding to metal surfaces and metal ions, which can provide enhanced corrosion inhibition as compared to many existing corrosion inhibitors. In addition, it is postulated that the compounds of formulae (I) and (II) form stable films because the compounds can form a 1,2-chelation complex with metal.

In certain embodiments, a compound of formula (I) or (II) provides lower corrosion rates for copper in the presence of oxidizing halogen compounds than commonly used corrosion inhibitors, such as tolyltriazole and benzimidazole. In certain embodiments, a compound of formula (I) or (II) provides a metal corrosion rate in the presence of an oxidizing halogen compound of about 0.2 mpy or less. In certain preferred embodiments, a compound of formula (I) or (II) provides a metal corrosion rate in the presence of an oxidizing halogen compound of about 0.1 mpy or less. Thus, in certain preferred embodiments, a compound of formula (I) or (II) provides a metal corrosion rate in the presence of an oxidizing halogen compound of about 0.1 mpy or less, about 0.05 mpy or less, about 0.04 mpy or less, about 0.03 mpy or less, about 0.02 mpy or less, about 0.01 mpy or less, about 0.005 mpy or less, or about 0.002 mpy or less.

In certain preferred embodiments, a compound of formula (I) or (II) inhibits corrosion of copper in the presence of oxidizing halogen compounds including, but not limited to, hypochlorite bleach, chlorine, bromine, hypobromite, hypochlorite, chlorine dioxide, iodine/hypoiodous acid, hypobromous acid, halogenated hydantoins, stabilized versions of hypochlorous or hypobromous acids, or combinations thereof. In certain preferred embodiments, the metal corrosion rate provided by a compound of formula (I) or (II) is essentially the same in the absence or presence of an oxidizing halogen compound.

In certain embodiments, a compound of formula (I) or (II) inhibits metal corrosion when added to an aqueous system comprising a non-halogen-containing oxidizing biocide including, but not limited to, peroxides (e.g., hydrogen peroxide), persulfates, permanganates, and peracetic acids.

Another advantage of the present methods is that a smaller amount of oxidizing halogen compound is required to maintain low microbial levels because the compounds of formulae (I) and (II) generally do not react with the oxidizing halogen compound. Furthermore, halogenated azoles that result from the reaction between an azole and oxidizing agent are known to be environmentally undesirable due to their toxicity. Thus, another advantage of the present methods is that the compounds of formulae (I) and (II) are resistant or essentially resistant to halogen attack, and do not lead to the release of halogenated azoles into the environment.

In certain preferred embodiments, the aqueous system is a cooling water system. The cooling water system can be a closed loop cooling water system or an open loop cooling water system. In certain preferred embodiments, a compound of formula (I) or (II) is added to a closed loop cooling water system at a dosage rate of from about 0.01 ppm to about 200 ppm. In certain preferred embodiments, a compound of formula (I) or (II) is added to an open loop cooling water system at a dosage rate of from about 0.01 ppm to about 20 ppm.

The compounds of formulae (I) and (II) are contacted with a metal surface by any suitable method. In certain embodiments, a solution of a compound of formula (I) or (II) is contacted with a metal surface by immersion, spraying, or other coating techniques. In certain preferred embodiments, a solution of a compound of formula (I) or (II) is introduced into the water of the aqueous system by any conventional method and is fed into the aqueous system on either a periodic or continuous basis.

In certain embodiments, if a compound of formula (I) or (II) is relatively insoluble in water, the compound may be made soluble by forming an organic or inorganic salt of the compound. Thus, in certain embodiments, a compound of formula (I) or (II) is a water-soluble salt. In certain embodiments, a compound of formula (I) or (II) is added as a solution in a water-miscible co-solvent including, but not limited to, acetone, methanol, ethanol, propanol, formic acid, formamide, propylene glycol, or ethylene glycol. In certain embodiments, a co-solvent is used to achieve maximum solubility of a compound of formula (I) or (II) in the aqueous system. In certain embodiments, low molecular weight polyethylene glycol, polypropylene glycol, a surfactant, or a combination thereof are used to increase the solubility of a compound of formula (I) or (II). In certain embodiments, a compound of formula (I) or (II) is present in an inorganic or organic solvent in an amount of from about 0.1 to 50 grams of compound per 100 mL of solution.

In another embodiment, the invention provides a formulation for inhibiting corrosion of a metal surface in contact with an aqueous system. The formulation comprises a compound of formula (I) or (II), a phosphoric acid, and a phosphinosuccinic oligomer. In a certain preferred embodiments, the phosphoric acid is orthophosphoric acid (i.e., phosphoric acid). In certain embodiments, the phosphinosuccinic oligomer is selected from the phosphinosuccinic oligomers as disclosed in U.S. Pat. No. 6,572,789, which is hereby incorporated by reference.

In certain preferred embodiments, the formulation comprises a compound of formula (I) wherein each X is the same or different, and is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl; Y is selected from the group consisting of hydroxyl, alkoxy, thiol, alkylthio, amino, and aminoalkyl; $R^1$ is selected from the group consisting of hydrogen, deuterium, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, hydroxyl, and carbonyl; $R^2$ is selected from the group consisting of hydrogen, aryl, heteroaryl, benzyl, alkylheteroaryl, $C_2$-$C_{16}$ alkenyl, $C_2$-$C_{16}$ alkynyl, $C_3$-$C_8$ cycloalkyl, and $C_1$-$C_{16}$ alkyl; and m is 1, 2, 3, or 4; or a salt thereof.

In certain preferred embodiments, the formulation comprises a compound of formula (II) wherein each of X and Y is the same or different, and is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl; R is selected from the group consisting of hydrogen, deuterium, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, hydroxyl, and carbonyl; m is 1, 2, 3, or 4; and n is 1, 2, 3, or 4; or a salt thereof.

In certain embodiments, the formulation further comprises a fluorescent organic compound. In certain preferred embodiments, the fluorescent organic compound is selected from the group consisting of Rhodamine, a derivative of Rhodamine, an acridine dye, fluorescein, a derivative of fluorescein, and combinations thereof. In certain embodiments, the formulation further comprises a fluorescent tagged polymer.

In certain embodiments, the formulation has a pH of from about 2 to about 5. Thus, in certain embodiments, the formulation has a pH of from about 2 to about 5, from about 2 to about 4, from about 2 to about 3, or from about 3 to about 5. In certain embodiments, the formulation has a pH of from about 11 to about 14. Thus, in certain embodiments, the formulation has a pH of from about 11 to about 14, from about 11 to about 13, from about 12 to about 14, or from about 13 to about 14.

Those skilled in the art will appreciate that a compound of formula (I) or (II) can be added to an aqueous system alone or in combination with other corrosion inhibitors or treatment chemicals. Multiple corrosion inhibitors can be dosed as a combined corrosion inhibitor formulation or each corrosion inhibitor can be added separately, including two or more compounds of formula (I) and/or formula (II). Moreover, a compound of formula (I) or (II) can be added to an aqueous system in combination with a variety of additional corrosion inhibitors including, but not limited to, triazoles, benzotriazoles (e.g., benzotriazole or tolyltriazole), benzimidazoles, orthophosphate, polyphosphates, phosphonates, molybdates, silicates, oximes, and nitrites. The compounds of formulae (I) and (II) also can be added to an aqueous system in combination with a variety of additional additives, such as treatment polymers, anti-microbial agents, anti-scaling agents, colorants, fillers, buffers, surfactants, viscosity modifiers, chelating agents, dispersants, deodorants, masking agents, oxygen scavengers, and indicator dyes.

The compounds of formulae (I) and (II) can be added to an aqueous system in any form. In certain embodiments, a compound of formula (I) or (II) is added to an aqueous system as a dried solid. In certain embodiments, a compound of formula (I) or (II) is added to an aqueous system as a solution in a co-solvent miscible with water. In certain preferred embodiments, a compound of formula (I) or (II) is added to an aqueous system as an aqueous solution.

In certain embodiments, a compound of formula (I) is added to a laundry system or a warewashing system.

In certain embodiments, a compound of formula (I) or (II) is added to an aqueous system that recirculates water. In certain embodiments, a compound of formula (I) or (II) is added to an aqueous system that has stagnant water.

The following examples further illustrate the invention but, of course, should not be construed as in any way limiting its scope.

Example 1

This Example illustrates a method of synthesis of compounds of formula (I) and (II) in accordance with an embodiment of the present invention.

General Chemistry Methods. The reactions were performed under positive pressure of nitrogen with oven-dried glassware. DL-mandelic acid, 4-methyl-o-phenylenediamine, 2-picolinic acid, hydrochloric acid, and polyphosphoric acid were purchased from Sigma-Aldrich (St. Louis, Mo.).

Synthesis of (5-methyl-1H-benzo[d]imidazol-2-yl)(phenyl)methanol

A roundbottom flask comprising 4-methyl-o-phenylenediamine (1.00 mmol, 122.2 g) and DL-mandelic acid (1.00 mol, 152.2 g) was charged with 200 mL aqueous hydrochloric acid (5N). The reaction mixture was refluxed at 100° C. for 6 hours. After completion, the reaction mixture was diluted with cold water and quenched with NaOH (10% aq. solution) until precipitation occurred. The precipitate was filtered and washed with cold water, yielding the title compound as a pink solid (202 g, 85%).

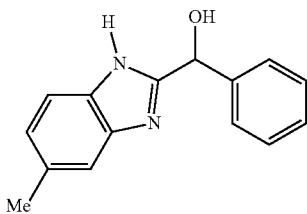 [SMILES: Cc1ccc2[nH]c(C(O)c3ccccc3)nc2c1]

Synthesis of 5-methyl-2-(2-Pyridyl)benzimidazole

A roundbottom flask was charged with 4-methyl-o-phenylenediamine (2.0 mmol, 2.40 g), 2-picolinic acid (1.98 mmol, 2.44 g), and polyphosphoric acid (19.3 g). The reaction mixture was heated at 160° C. for 5 hours. After completion, the reaction mixture was poured into cold water and neutralized with an aqueous $NH_4OH$ solution. The mixture was stirred overnight. The precipitate was filtered and washed with cold water, yielding the title compound as a brown solid (2.82 g, 68%).

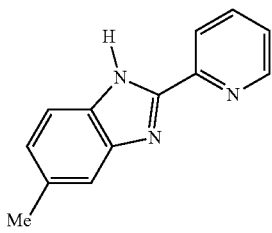 [SMILES: Cc1ccc2[nH]c(-c3ccccn3)nc2c1]

Example 2

This Example illustrates the corrosion rate of copper using a method of an embodiment of the present invention.

The corrosion rate of copper in the presence of (1H-benzo[d]imidazol-2-yl)(phenyl)methanol, (5-methyl-1H-benzo[d]imidazol-2-yl)(phenyl)methanol, 2-(2-pyridyl)benzimidazole, 5-methyl-2-(2-pyridyl)benzimidazole, 2-(3-pyridyl)benzimidazole, and 2-(4-pyridyl) benzimidazole was determined using linear polarization resistance measurements. In addition, the corrosion rate of copper in the presence of known corrosion inhibitors benzimidazole, 2-phenylbenzimidazole, and tolyltriazole was determined using linear polarization resistance measurements. The compounds of formulae (I) and (II) were prepared as disclosed in Example 1. Benzimidazole, 2-phenylbenzimidazole, and tolyltriazole were purchased from Sigma-Aldrich (St. Louis, Mo.). For each experiment, cylindrical copper coupons pre-polished using SIC 600 paper and fitted on a Pine rotator were immersed in a solution of corrosion inhibitor. The test solution comprised 470 ppm calcium, 230 ppm magnesium, 590 ppm chloride, 260 ppm sulfate, and 100 ppm alkalinity, as $CaCO_3$. The pH of the test water was maintained at 7.0 using carbon dioxide, and the water temperature was maintained at 45° C. throughout the experiment.

The copper samples were immersed in 1 liter electrochemical cells comprising a 5 ppm inhibitor solution, and the Rp (polarization resistance) was recorded over a 20 to 24 hour period. The analysis was conducted using the following testing conditions: Initial E: −0.02V; Final E: +0.02V; Scan rate: 0.5 mV/s; Sample period: 1 second; Repeat time: 15 minutes; Sample area: 5 $cm^2$; Density: 8.92 $g/cm^3$; Copper Eq. Weight: 63.54 g; and Initial delay: 30 seconds.

Figure 2:
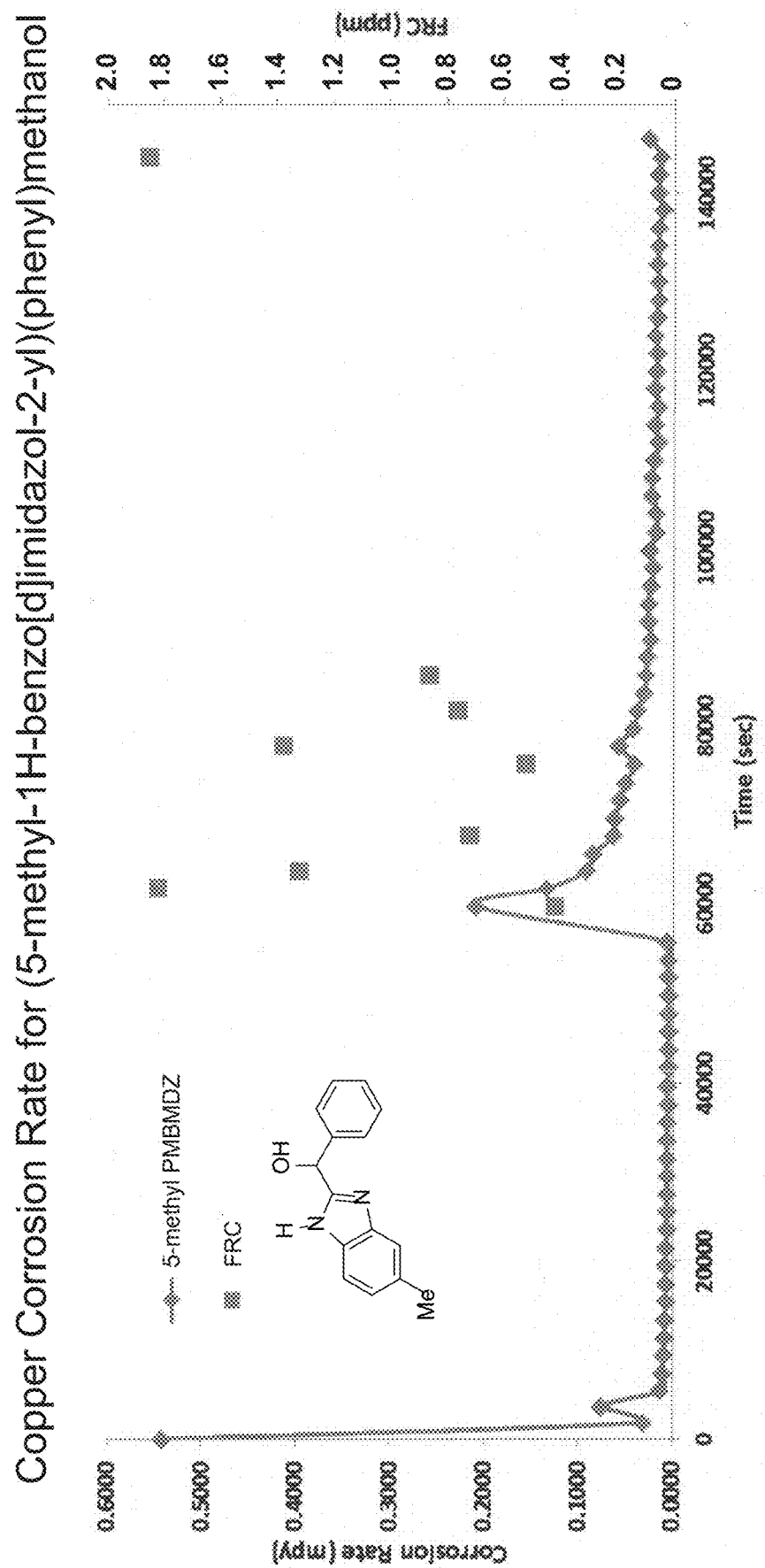
FIG. 2 is a line graph that illustrates the corrosion rate of copper using (5-methyl-1H-benzo[d]imidazol-2-yl)(phenyl) methanol as a corrosion inhibitor in the absence and presence of bleach.
Figure 3:
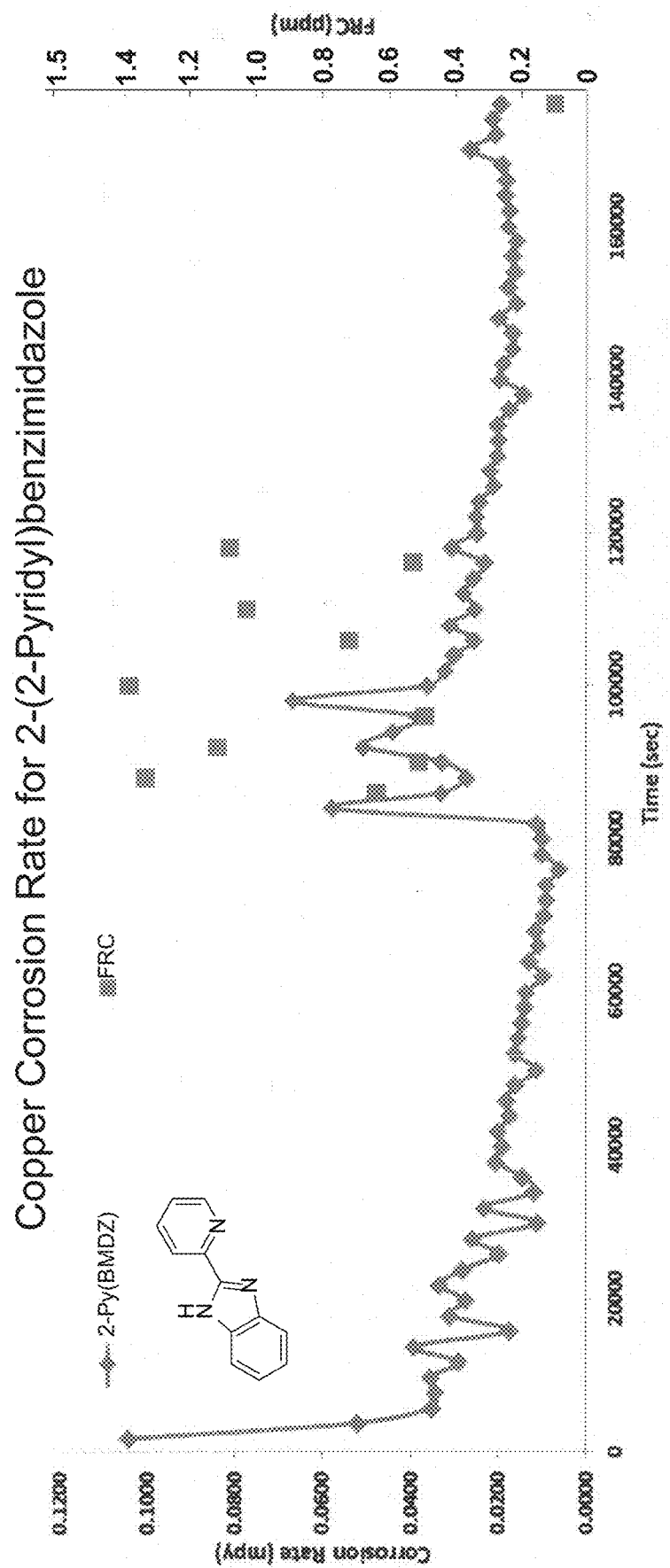
FIG. 3 is a line graph that illustrates the corrosion rate of copper using 2-(2-pyridyl)benzimidazole as a corrosion inhibitor in the absence and presence of bleach.
Figure 4:
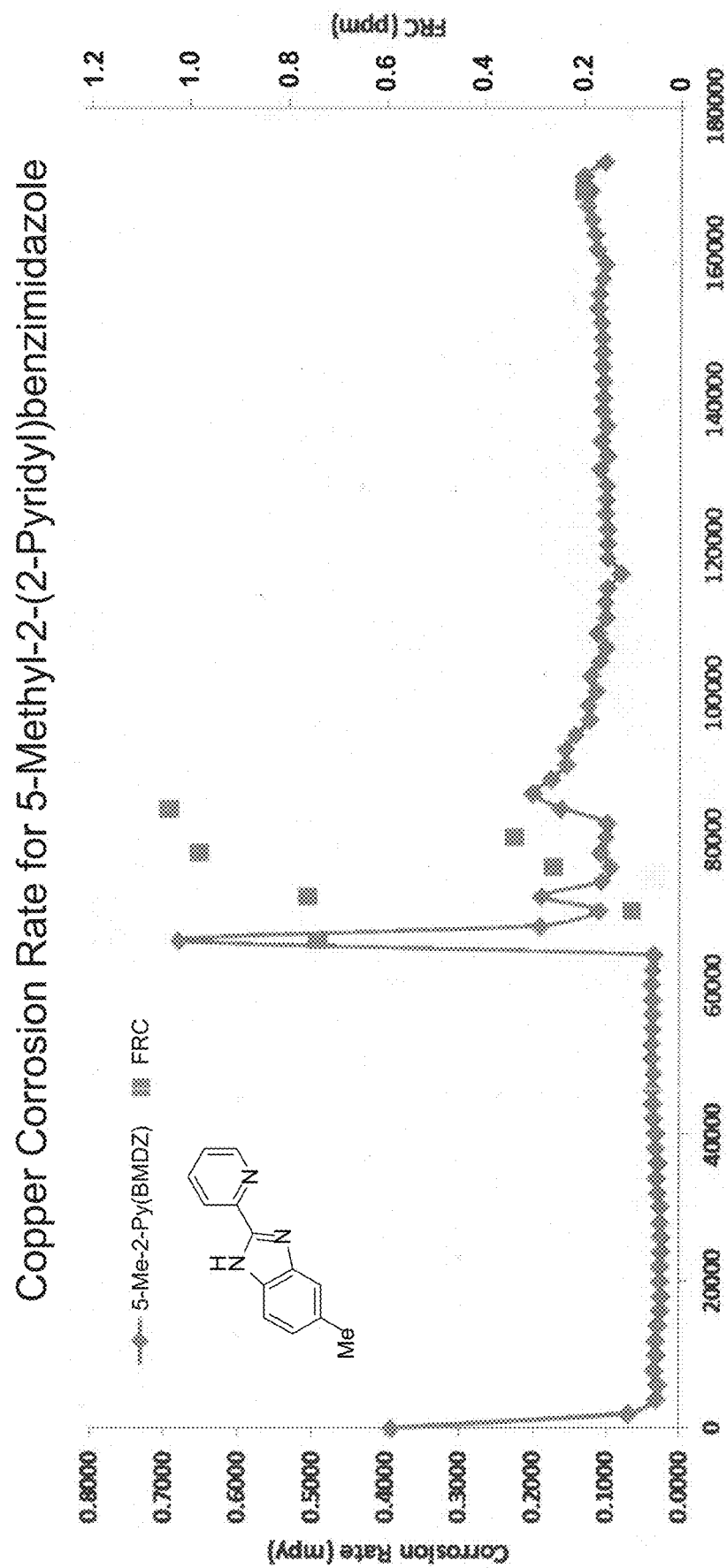
FIG. 4 is a line graph that illustrates the corrosion rate of copper using 5-methyl-2-(2-pyridyl)benzimidazole as a corrosion inhibitor in the absence and presence of bleach.
Figure 5:
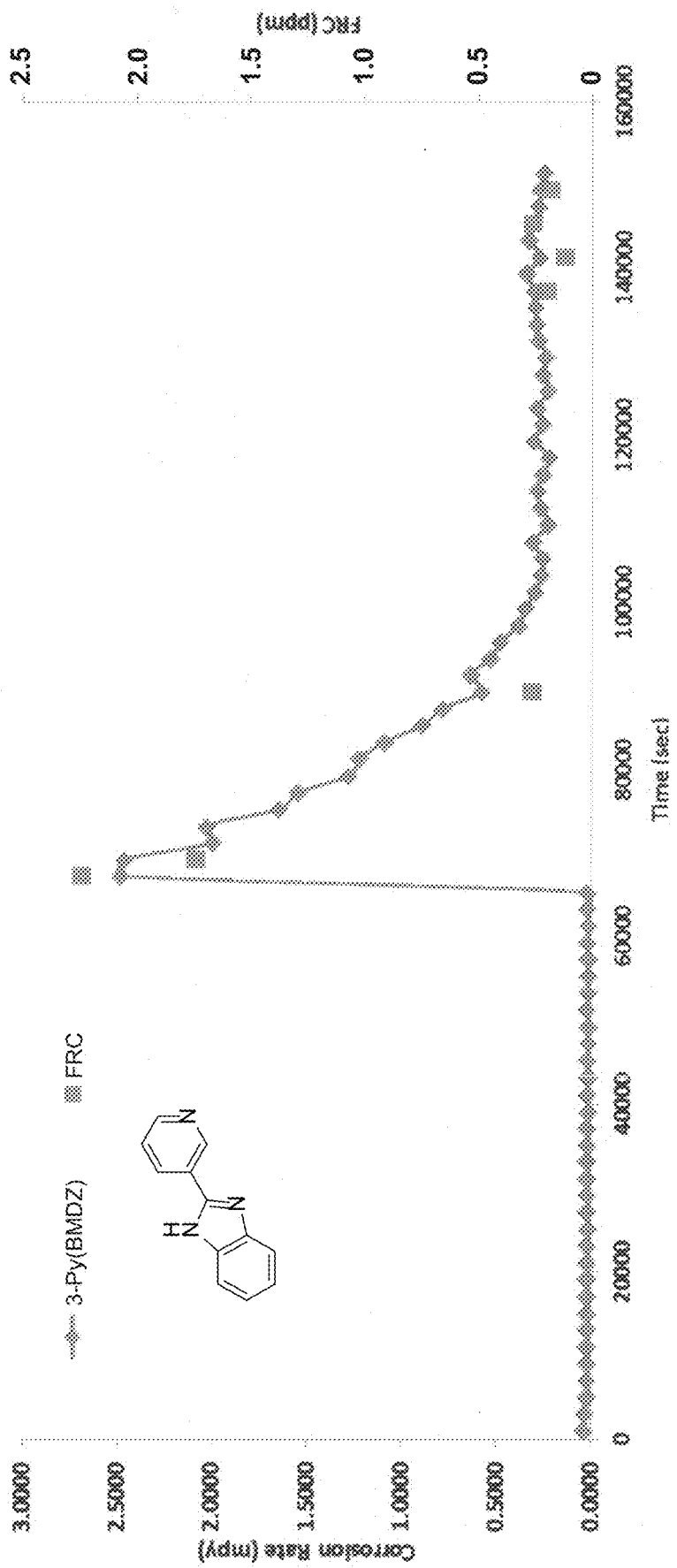
FIG. 5 is a line graph that illustrates the corrosion rate of copper using 2-(3-pyridyl)benzimidazole as a corrosion inhibitor in the absence and presence of bleach.
Figure 6:
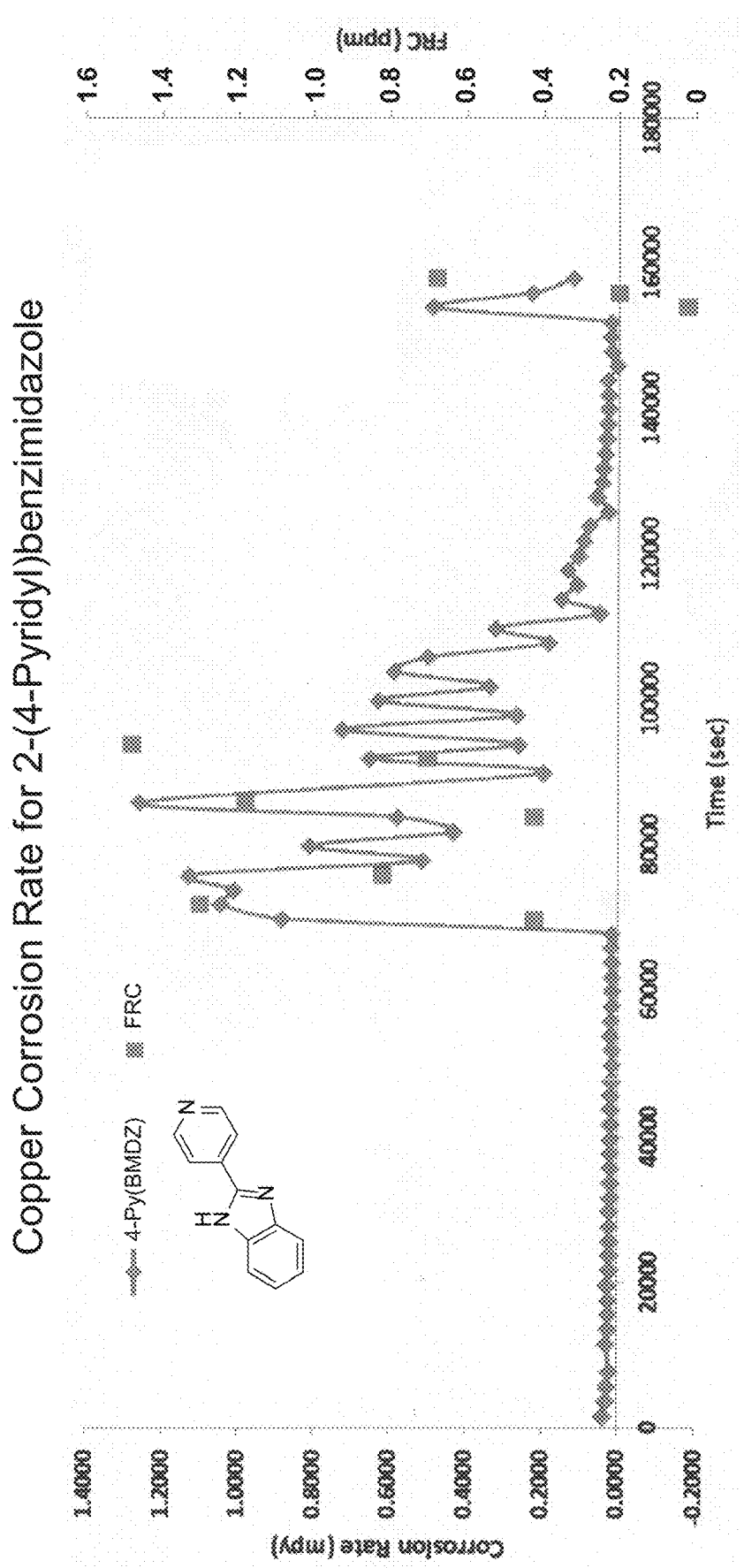
FIG. 6 is a line graph that illustrates the corrosion rate of copper using 2-(4-pyridyl)benzimidazole as a corrosion inhibitor in the absence and presence of bleach.
Figure 7:
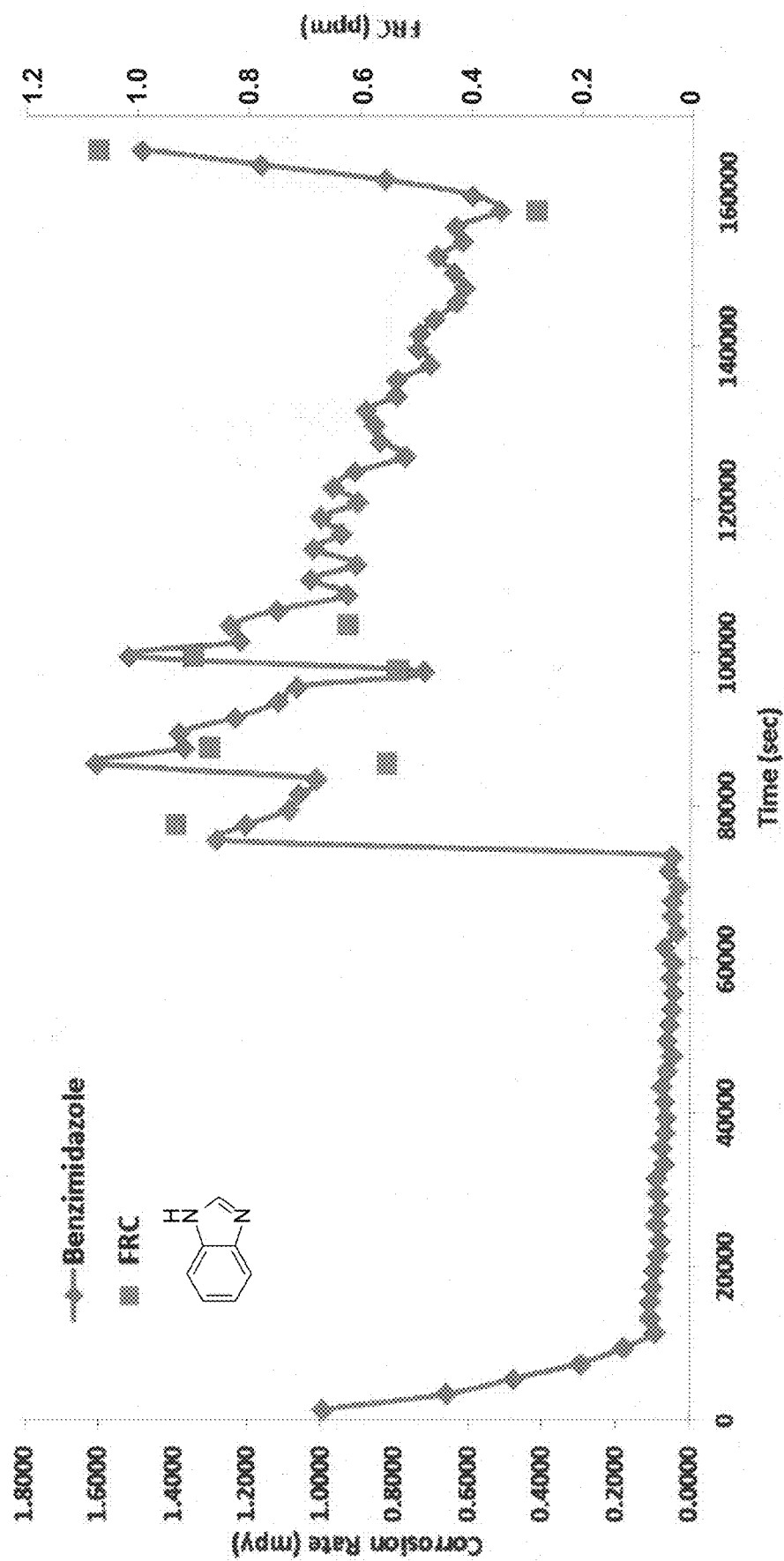
FIG. 7 is a line graph that illustrates the corrosion rate of copper using benzimidazole as a corrosion inhibitor in the absence and presence of bleach.
Figure 8:
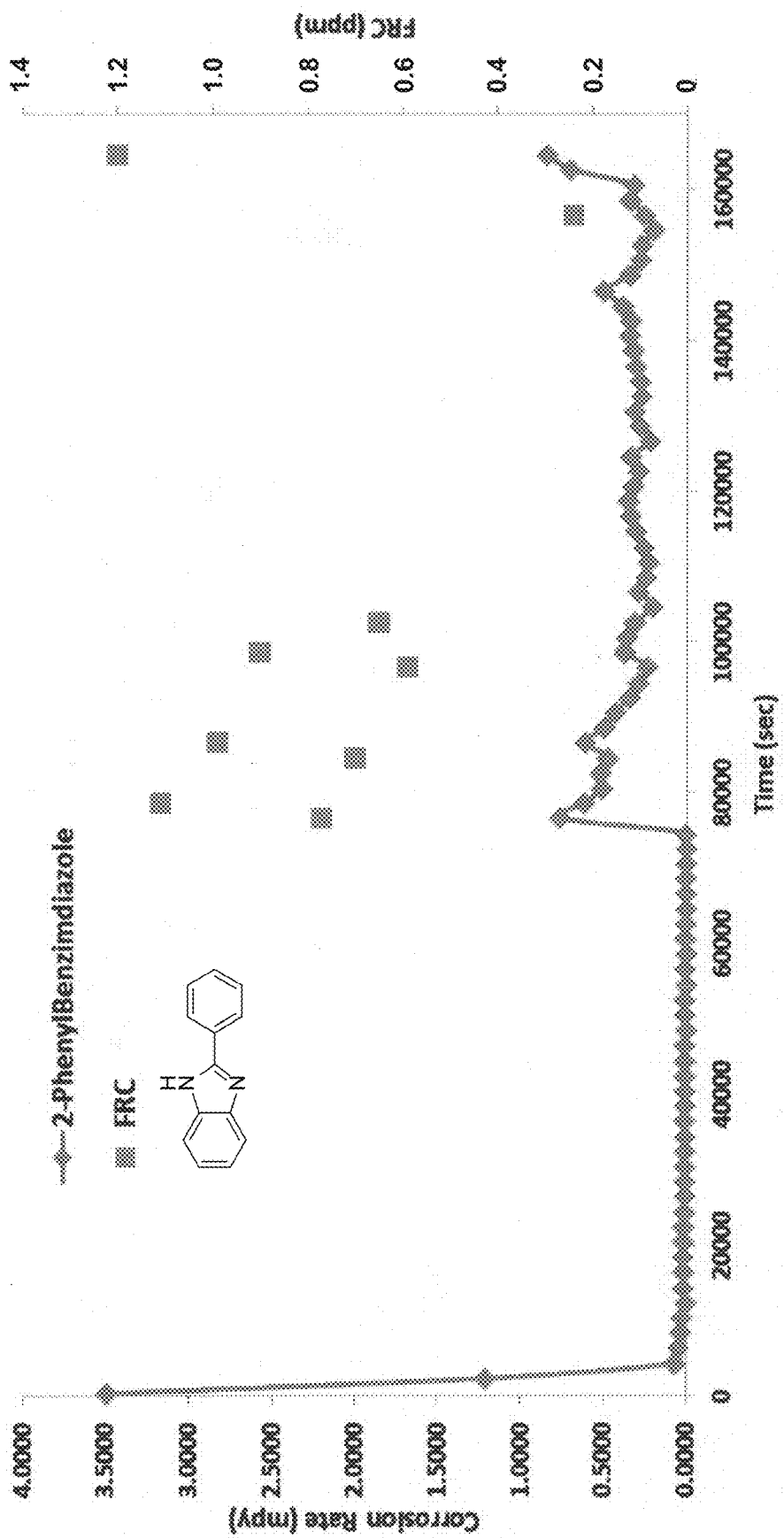
FIG. 8 is a line graph that illustrates the corrosion rate of copper using 2-phenylbenzimidazole as a corrosion inhibitor in the absence and presence of bleach.

Next, the copper samples were exposed to a 25% bleach solution. After the FRC reached 1 ppm, the copper samples were analyzed. Throughout the analysis, the bleach solution was maintained at 1 ppm FRC. The Rp in the absence and presence of bleach was collected and analyzed, and the average corrosion rate was calculated and recorded in Table 1. Corrosion rates were calculated in mils per year (mpy). FIGS. 1-8 display data plots for compounds 1-8.

As shown in Table 1 and FIGS. 1-6, compounds of formulae (I) and (II) (e.g., compounds 1-6) greatly decrease the corrosion rate of copper. Moreover, the corrosion rate of copper in the presence of compounds 1 and 2 is lower than in the presence of benzimidazole and commonly used tolyltriazole. The corrosion rate of copper in the presence of the pyridylbenzimidazoles (e.g., compounds 3-6) was lower than benzimidazole and comparable to commonly used tolyltriazole.

Upon the addition of bleach, the corrosion rate of copper increased only slightly in the presence of (1H-benzo[d]imidazol-2-yl)(phenyl)methanol and (5-methyl-1H-benzo[d]imidazol-2-yl)(phenyl)methanol. The corrosion rate of copper in the presence of 2-(2-pyridyl)benzimidazole remained nearly constant in the presence of bleach (0.018 mpy vs. 0.030 mpy). It was surprisingly and unexpectedly found that proximity of the pyridyl nitrogen to the benzimidazole ring affected the corrosion rate. For example, it was observed that pyridal rings substituted at the 3- and 4-positions yield higher copper corrosion rates than 2-(2-pyridyl)benzimidazoles in the presence of bleach (compounds 5 and 6 vs. compounds 3 and 4). The data suggests that the 2-pyridyl nitrogen may impart greater film stability due to 1,2-chelation with the metal surface. Overall, compounds 1-6 provide greater corrosion protection for copper than benzimidazole. Compounds 1-3 provide greater corrosion protection for copper than commonly used tolyltriazole in the presence of bleach.

This Example illustrates that a method of the present invention can greatly reduce the rate of copper corrosion. Moreover, this Example illustrates that a method of the present invention can provide greater corrosion resistance in the presence of an oxidizing halogen compound than commonly used corrosion inhibitors such as tolyltriazole.

TABLE 1

| Compound No. | Compound Name | No FRC Corrosion Rate (mpy) | 1 ppm FRC Corrosion Rate (mpy) |
|---|---|---|---|
| 1 | (1H-benzo[d]imidazol-2-yl)(phenyl)methanol | 0.0058 | 0.0210 |
| 2 | (5-methyl-1H-benzo[d]imidazol-2-yl)(phenyl)methanol | 0.0078 | 0.024 |
| 3 | 2-(2-Pyridyl)benzimidazole | 0.018 | 0.030 |
| 4 | 5-Methyl-2-(2-Pyridyl)benzimidazole | 0.032 | 0.127 |
| 5 | 2-(3-Pyridyl)benzimidazole | 0.020 | 0.347 |
| 6 | 2-(4-Pyridyl)benzimidazole | 0.018 | 0.254 |
| 7 | Benzimidazole (BMDZ) | 0.0890 | 0.9594 |
| 8 | 2-phenylbenzimidazole | 0.0128 | 0.3726 |
| 9 | Tolyltriazole (TT) | 0.0214 | 0.0995 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A formulation for inhibiting corrosion of a metal surface, the formulation comprising one or more phosphorus-containing compounds and a compound of formula (I) or (II);

wherein formula (I) is

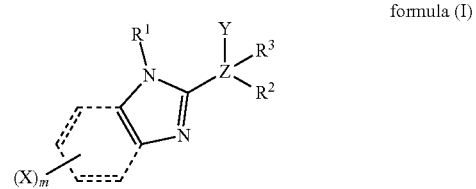

formula (I)

wherein each X is the same or different, and each is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl;

Y is selected from the group consisting of hydroxyl, halogen, oxo, alkoxy, thiol, alkylthio, amino, hydrogen, and aminoalkyl;

Z is selected from the group consisting of carbon and nitrogen;

$R^1$ is selected from the group consisting of hydrogen, deuterium, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, hydroxyl, and carbonyl;

$R^2$ and $R^3$ are selected from the group consisting of hydrogen, halogen, hydroxyl, aryl, phenyl, heteroaryl, benzyl, alkylheteroaryl, carbonyl, $C_2$-$C_{16}$ alkenyl, $C_2$-$C_{16}$ alkynyl, $C_3$-$C_8$ cycloalkyl, and $C_1$-$C_{16}$ alkyl; and m is 1, 2, 3, or 4; or a salt thereof; and formula (II) is

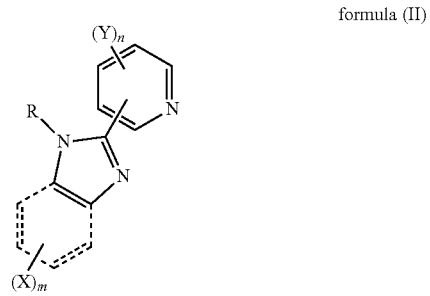

formula (II)

wherein each of X and Y is the same or different, and each is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl;

R is selected from the group consisting of hydrogen, deuterium, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, hydroxyl, and carbonyl;

m is 1, 2, 3, or 4; and
n is 1, 2, 3, or 4; or
a salt thereof;
with the proviso that when the imidazole is benzimidazole and X and R are both hydrogen, then the pyridine ring is 2-pyridyl.

2. The formulation of claim 1, wherein the one or more phosphorus-containing compounds is selected from phosphoric acid, polyposphoric acid, phosphorus pentoxide, and a phosphinosuccinic oligomer.

3. The formulation of claim 2, wherein the one or more phosphorus-containing compounds is polyposphoric acid.

4. The formulation of claim 1, wherein the formulation has a pH of from about 2 to about 5.

5. The formulation of claim 4, wherein the formulation has a pH of from about 2 to about 4.

6. The formulation of claim 5, wherein the formulation has a pH of from about 2 to about 3.

7. The formulation of claim 1, wherein the formulation comprises a compound of formula (I), wherein the compound of formula (I) is

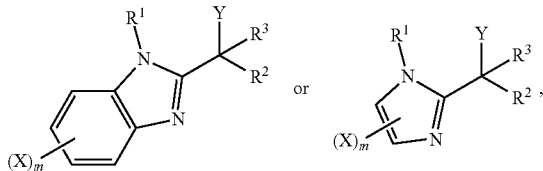

wherein each X is the same or different, and each is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl;

Y is selected from the group consisting of hydroxyl, halogen, oxo, alkoxy, thiol, alkylthio, amino, hydrogen, and aminoalkyl;

$R^1$ is selected from the group consisting of hydrogen, deuterium, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, hydroxyl, and carbonyl;

$R^2$ and $R^3$ are the same or different, and each is selected from the group consisting of hydrogen, halogen, hydroxyl, aryl, phenyl, heteroaryl, benzyl, alkylheteroaryl, carbonyl, $C_2$-$C_{16}$ alkenyl, $C_2$-$C_{16}$ alkynyl, $C_3$-$C_8$ cycloalkyl, and $C_1$-$C_{16}$ alkyl; and m is 1, 2, 3, or 4; or
a salt thereof.

8. The formulation of claim 7, wherein the compound of formula (I) is

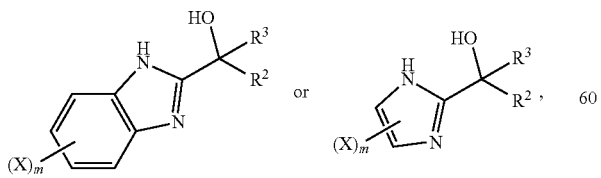

wherein each X is the same or different, and each is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl;

$R^2$ and $R^3$ are the same or different, and each is selected from the group consisting of hydrogen, halogen, hydroxyl, aryl, phenyl, heteroaryl, benzyl, alkylheteroaryl, carbonyl, $C_2$-$C_{16}$ alkenyl, $C_2$-$C_{16}$ alkynyl, $C_3$-$C_8$ cycloalkyl, and $C_1$-$C_{16}$ alkyl; and m is 1, 2, 3, or 4; or
a salt thereof.

9. The formulation of claim 8, wherein the compound of formula (I) is

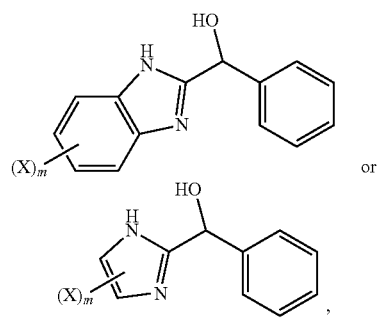

wherein each X is the same or different, and each is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl; and m is 1, 2, 3, or 4; or
a salt thereof.

10. The formulation of claim 9, wherein the compound of formula (I) is

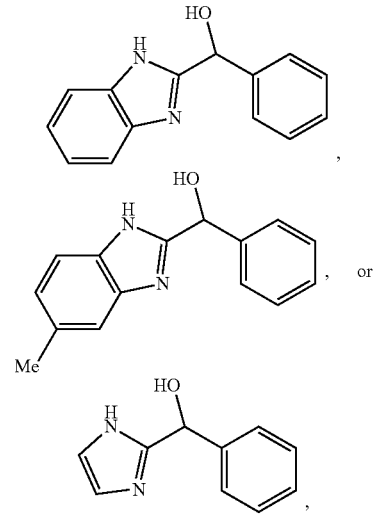

or a salt thereof.

11. The formulation of claim 1, wherein the formulation comprises a compound of formula (II), wherein the compound of formula (II) is

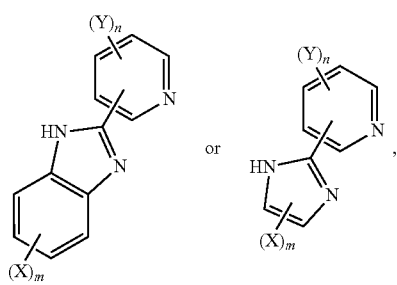

wherein each of X and Y is the same or different, and each is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl;

m is 1, 2, 3, or 4; and n is 1, 2, 3, or 4; or a salt thereof, with the proviso that when X is hydrogen, then the pyridine ring is 2-pyridyl.

12. The formulation of claim 11, wherein the compound of formula (II) is

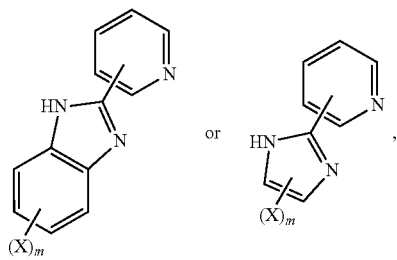

wherein each X is the same or different, and each is selected from the group consisting of hydrogen, $C_1$-$C_{16}$ alkyl, aryl, $C_2$-$C_{16}$ alkenyl, $C_2$-$C_{16}$ alkynyl, heteroaryl, $C_3$-$C_8$ cycloalkyl, benzyl, alkylheteroaryl, halogen, halosubstituted alkyl, amino, aminoalkyl, cyano, alkoxy, hydroxyl, thiol, alkylthio, carbonyl, nitro, phosphoryl, phosphonyl, and sulfonyl; and m is 1, 2, 3, or 4; or a salt thereof, with the proviso that when X is hydrogen, then the pyridine ring is 2-pyridyl.

13. The formulation of claim 12, wherein the compound of formula (II) is

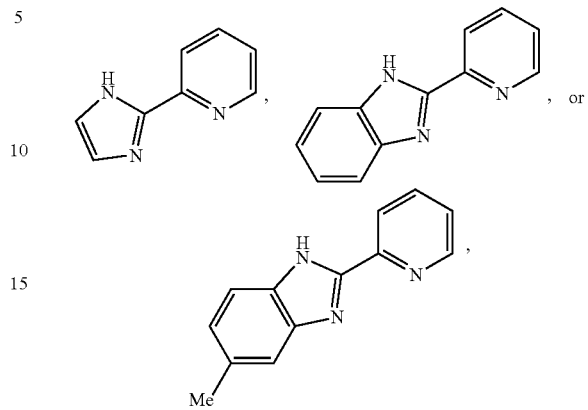

or a salt thereof.

14. The formulation of claim 1, wherein the formulation further comprises a fluorescent organic compound.

15. The formulation of claim 14, wherein the fluorescent organic compound is selected from the group consisting of Rhodamine, a derivative of Rhodamine, an acridine dye, fluorescein, a derivative of fluorescein, and combinations thereof.

16. The formulation of claim 1, wherein the formulation further comprises one or more additives selected from treatment polymers, anti-microbial agents, anti-scaling agents, colorants, fillers, buffers, surfactants, viscosity modifiers, chelating agents, dispersants, deodorants, masking agents, oxygen scavengers, and indicator dyes.

17. The formulation of claim 16, wherein the formulation further comprises one or more anti-scaling agents.

18. The formulation of claim 16, wherein the formulation further comprises one or more treatment polymers.

19. The formulation of claim 16, wherein the formulation further comprises one or more dispersants.

20. The formulation of claim 1, wherein the formulation further comprises one or more additional corrosion inhibitors selected from triazoles, benzotriazoles, benzimidazoles, orthophosphate, polyphosphates, phosphonates, molybdates, silicates, oximes, and nitrites.

\* \* \* \* \*

UNITED STATES PATENT AND TRADEMARK OFFICE
CERTIFICATE OF CORRECTION

PATENT NO. : 11,306,400 B2
APPLICATION NO. : 16/225293
DATED : April 19, 2022
INVENTOR(S) : Rane et al.

It is certified that error appears in the above-identified patent and that said Letters Patent is hereby corrected as shown below:

In the Claims

Claim 2, Column 23, Line 9, delete "polyposphoric" and insert --polyphosphoric--.

Claim 3, Column 23, Line 12, delete "polyposphoric" and insert --polyphosphoric--.

Signed and Sealed this
Twenty-eighth Day of June, 2022

*Katherine Kelly Vidal*

Katherine Kelly Vidal
*Director of the United States Patent and Trademark Office*